(12) United States Patent
Forde

(10) Patent No.: US 12,239,773 B2
(45) Date of Patent: Mar. 4, 2025

(54) BUBBLE TRAP DEVICE

(71) Applicant: TESSEN SOLUTIONS LIMITED, Bishopstown (IE)

(72) Inventor: Vincent Forde, Carrigaline (IE)

(73) Assignee: TESSEN SOLUTIONS LIMITED, Bishopstown (IE)

( * ) Notice: Subject to any disclaimer, the term of this patent is extended or adjusted under 35 U.S.C. 154(b) by 793 days.

(21) Appl. No.: 17/421,524

(22) PCT Filed: Jan. 30, 2019

(86) PCT No.: PCT/EP2019/052299
§ 371 (c)(1),
(2) Date: Jul. 8, 2021

(87) PCT Pub. No.: WO2020/156666
PCT Pub. Date: Aug. 6, 2020

(65) Prior Publication Data
US 2022/0088282 A1    Mar. 24, 2022

(51) Int. Cl.
*A61M 5/38* (2006.01)
*A61M 1/36* (2006.01)
(Continued)

(52) U.S. Cl.
CPC ........ *A61M 1/3633* (2013.01); *A61M 5/1411* (2013.01); *A61M 5/165* (2013.01); *A61M 5/38* (2013.01)

(58) Field of Classification Search
CPC .. A61M 1/3633; A61M 5/1411; A61M 5/165; A61M 5/38; A61M 5/385;
(Continued)

(56) References Cited

U.S. PATENT DOCUMENTS 3,827,561 A    8/1974    Aid et al.
4,048,995 A    9/1977    Mittleman
(Continued)

FOREIGN PATENT DOCUMENTS

CA        986029 A     3/1976
CN     107666922 A     2/2018
(Continued)

OTHER PUBLICATIONS

International Search Report issued in PCT/EP2019/052299; mailed Nov. 21, 2019.
(Continued)

*Primary Examiner* — Nathan R Price
*Assistant Examiner* — Haden Matthew Ritchie
(74) *Attorney, Agent, or Firm* — Bookoff McAndrews, PLLC

(57) ABSTRACT

The present invention is directed to an apparatus suitable for separating and collecting gas bubbles entrained in a liquid, wherein the apparatus comprises a housing defining at least one chamber, the chamber having an inlet port and an outlet port; a diverter positioned between the inlet port and the outlet port; and, an elongated exit tube with an intake end and an export end; wherein the intake end of the elongated exit tube is centrally located within the chamber and the export end of the elongated exit tube is connected to the outlet port of the chamber.

19 Claims, 16 Drawing Sheets

(51) Int. Cl.
*A61M 5/14* (2006.01)
*A61M 5/165* (2006.01)
*A61M 5/36* (2006.01)

(58) Field of Classification Search
CPC ... A61M 5/35; A61M 1/3627; B01D 19/0031; B01D 19/0042
See application file for complete search history.

(56) References Cited

U.S. PATENT DOCUMENTS

| | | | |
|---|---|---|---|
| 4,382,900 A | 5/1983 | Wem | |
| 5,143,607 A * | 9/1992 | Bernhardt | B01D 19/0005 166/278 |
| 5,674,199 A * | 10/1997 | Brugger | A61M 1/3627 604/122 |
| 6,508,859 B1 | 1/2003 | Zia et al. | |
| 6,537,356 B1 | 3/2003 | Soriano | |
| 7,141,097 B2 | 11/2006 | Leahey | |
| 7,279,031 B1 * | 10/2007 | Wright | A61M 1/3627 96/197 |
| 8,632,624 B2 * | 1/2014 | Cassidy | A61M 1/3638 604/122 |
| 9,533,109 B2 * | 1/2017 | Bryan | A61M 1/3627 |
| 2005/0247198 A1 | 11/2005 | Kent | |
| 2006/0173395 A1 | 8/2006 | Brugger et al. | |
| 2011/0190700 A1 * | 8/2011 | Kavazov | A61M 5/385 604/152 |
| 2016/0095987 A1 * | 4/2016 | Chattaraj | A61M 39/10 604/126 |
| 2016/0346485 A1 | 12/2016 | Mohr et al. | |
| 2022/0001105 A1 * | 1/2022 | Shmilovich | A61M 5/16827 |

FOREIGN PATENT DOCUMENTS

| | | |
|---|---|---|
| EP | 0423841 A1 | 4/1991 |
| EP | 2463004 A1 | 6/2012 |
| GB | 2059776 A | 4/1981 |
| GB | 2495625 A | 4/2013 |
| JP | 2004122066 A | 4/2004 |
| JP | 2010064007 A | 3/2010 |
| WO | 2005053772 A1 | 6/2005 |
| WO | 2011128850 A2 | 10/2011 |
| WO | 2020156666 A1 | 8/2020 |
| WO | 2022023079 A1 | 2/2022 |

OTHER PUBLICATIONS

International Search Report in corresponding Application No. PCT/EP2023/052032, dated Apr. 21, 2023, (7 pages).
European Search Report in corresponding EP Application No. 24178297.8, dated Aug. 8, 2024, (10 pages).
Japanese Office Action in corresponding JP Application dated Sep. 4, 2024, (5 pages).

* cited by examiner

BUBBLE TRAP DEVICE

INTRODUCTION

This invention relates to a bubble trap suitable for separating and collecting gas bubbles present in a fluid. A fluid is a substance that naturally deforms (flows) under applied shear stress. Fluids are a phase of matter and include liquids, gases and plasma.

Gases are naturally present in fluids. Such gases entrained in a fluid tend to be unstable due to various environmental factors such as flow rate, temperature, chemical reactions, turbulence, motion and friction. Unstable gases tend to degas from a liquid solution, meaning that they separate from the liquid fraction resulting in the formation of gas bubbles. Bubbles of various sizes may form as a result of the degassing phenomenon and flow freely within the fluid such that they may be carried, under force, in the direction of the fluid flow. Gas bubbles naturally float upwards and have a propensity to coalesce such that, where provided with the opportunity, the gas will come together to form essentially one large gas bubble.

Bubbles of gas are fluid in that they flow and deform. Gas bubbles maintain structure due to the combination of the internal pressure of the gas pushing outwards on the gas bubble membrane and the external liquid pressures pushing inward on the gas bubble membrane. Low external liquid pressure is experienced on the uppermost portion of the bubble membrane while higher external liquid pressure is exerted on the bottommost portion of the bubble membrane. As such, gas bubbles tend to rise in response to this external liquid pressure profile.

A gas bubble endeavours to maintain integral shape; however, it may become deformed and elongated under duress, such as being sucked into a narrow tube. The gas bubble will try to return to a rounder ball shape where possible, unless restricted, such as happens in tubing. Gas bubbles therefore tend to adhere to the internal walls of long tubing and deform from the preferred round shape to an elongated oval shape.

The flow rate into and out of any degassing chamber must be equal to ensure the correct dosing regimen of medication to the patient. Any restriction to flow through the degassing chamber will affect the dosing regimen. This is of particular importance for certain medications with a narrow therapeutic window, wherein the smallest deviation in the dosing regimen could become toxic to the patient.

One such scenario where gas bubbles entrained in a fluid degas from solution and cause an issue is in Intravenous (IV) drip set-ups. A typical IV drip set-up 100 used in hospitals is shown in FIG. 1. Such an IV drip set-up 100 comprises and IV pole 102, from which a primary IV drip bag 104 is suspended via an extender 106. The primary IV drip bag 104 also has an injection port 108, which is used to add additional last-minute components to the IV drip solution contained within the primary IV drip bag 104. The primary IV drip bag 104 is connected to primary IV tubing 110. The primary IV tubing 110 typically comprises a sterile spike 112, a drip chamber 114, a back-check valve 116, at least one port 118 120, a slider clamp 122 and a roller clamp 124. The primary IV tubing 110 is connected to extension tubing 126 via a luer lock 128. While a luer lock has been described, it is to be appreciated that other securing means, such as a push-fit connection, may also be used. The extension tubing 126 connects to a cannula 130 and may also comprise a clamp 132. The typical IV drip set-up 100 may optionally comprise a secondary IV drip bag 134 suspended from a hook 136 of the IV pole 102, with a secondary injection port 138, sterile spike 140 and drip chamber 142. The secondary IV drip bag 134 is connected, via the at least one port 118 to the primary IV tubing 110 via secondary tubing 144.

In use, the liquid solution in the IV drip typically flows under the influence of a gravity pressure gradient (i.e. from high pressure to low pressure) from the IV drip bag 104 suspended from the top of the IV pole 102, through to the cannula 130, wherein the IV drip solution enters the blood stream of the patient, the patient generally being positioned lower than the IV drip bag 104.

While this typical IV drip set-up shows a gravity pressure gradient to be used, machine induced pressure gradients (e.g. IV pumps) may also be used to control flow rates.

In IV drips entrained gas degasses from the liquid solution of the IV drip as it travels from an IV drip bag 104, 134 to the cannula 130, wherein the liquid solution of the IV drip enters the blood stream of the patient. Any air, or gas, that enters the bloodstream will likely result in an embolism as gas bubbles can cause an occlusion that prevents blood flow. Vascular Air Embolism (VAE) or induced Vascular Air Embolism can occur when gas bubbles enter the venous system, often because of an IV fluid infusion procedure, which is a common method of delivering fluids to a patient. Further complications can occur because of VAE, such as heart arrhythmia, heart attack, stroke and death. Another complication of micro or macro bubbles entering the blood stream is Haemolysis, where the blood cells are broken down, leading to further strain on the body and increased recovery time for patients. It is therefore important to remove any air/gas that degasses from the solution before the gas bubbles have the chance to enter the bloodstream.

Throughout this specification, the term "liquid" shall be understood to encompass any type of liquid solution, liquid medication, or other liquids intended for intravenous delivery or other liquid-like materials such as blood, liquid supplements, parenteral nutrition, suspensions, bodily fluids, or other similarly viscous material suitable for transfusion or intravenous delivery.

Throughout this specification, the term "fluid" shall be understood to encompass both a liquid phase and a gas phase, wherein the gas is entrained or introduced to the liquid phase.

In IV drip set-ups it is common to include a drip chamber 114, sometimes referred to as a 'Murphy Dropper' device. A Murphy Dropper 114 has dual functionality in that it first enables observation of the fluid flow rate and secondly to remove risk of air or gas that may have formed in the bag from entering the flexible tubing. Such drip chambers 114 may have a ball that floats on the fluid, the purpose of which is to block the entrance to the flexible tube should the bag 104,134 empty of fluids, a situation which could cause an excess of air to become entrained in the line. This air would present a serious complication to a patient if the line was placed in the vein and the entrained air was not observed. Drip chambers 114, such as the Murphy Dropper tend to be located at the top of the line, just below the IV drip bag 104, 134. This position is intentional to enable ease of access and means to manually purge the drip chamber 114 of air that has collected therein. However, the position is furthest from the entry point to the patient (i.e. the cannula 130) and degassing of fluids and entrainment of air is possible throughout the length of the line, meaning that it is possible for air bubbles to form after the solution has passed through the drip chamber 114 and enter the bloodstream via the cannula 130 into the patient's vein.

Such IV drip set-ups typically require constant visual monitoring and manual removal of the gas bubbles, which is time-consuming, labour-intensive and erratic, subject to human error. Removal of bubbles tends to require removal of a proportion of the IV drip solution to ensure the gas does not enter the body of the patient, which is wasteful of hospital resources.

Often, electronic bubble monitors are attached to IV tube to aid in the identification of gas bubbles. These monitors give an audible alarm intended to alert adjacent clinical staff to the risk and often the bubble monitor will stop the flow of the fluids to enable removal by a medical professional. Persistent stoppage of the flow of IV fluids can be problematic for the patient and increases workloads for staff. Application of these expensive and cumbersome devices can be further limited by location, availability of power sources, training requirements, maintenance issues or lack of resources.

In surgical procedures it is common for fluids to be warmed to align with body temperatures to combat the effects of vasodilation due to anaesthetic. As the solubility of gases decreases as temperature increases, the heated fluids become unstable quickly and this can lead to large volumes of gas bubbles forming right throughout the length of the IV tube. Extra vigilance is required to observe and remove the risk of VAE during these procedures, with increasing time losses in the expensive surgical environment.

It is common for extension tubing to be added to an IV set in situations where the location of the IV stand is inconvenient to have near to the bed, typically during surgeries with multiple staff present. In this case, the extended tubing may provide further challenges for clinical staff to observe the bubbles contained within the tube and also gives additional volume of fluids from which gas can defuse.

Ingress of air can also occur in IV tubing at port sites, joining locations or valves due to poor sealing of the joints or improper venting of gas during priming by staff. Air can be further introduced into the closed system by staff injecting supplementary medications into the infusion liquid solution at any location between the IV bag and the point of entry into the patient.

Another such scenario where gas bubbles entrained in a fluid degas from solution and cause an issue is in blood transfusion and extracorporeal blood treatment set-ups. These set-ups have many similar features to IV set-up and as such experience much the same issues. In addition, extra care is needed in collecting, handling and treatment of blood fluids as phlebotomists will reject poor quality blood. External stress on the blood cells, such as turbulence, friction and impacts, can cause haemolysis. Furthermore, blood, sources are scarce and expensive.

Removing gas entrained in, or introduced into, a liquid is a long-standing problem, of which many different means of removing said gas have been tried, for example U.S. Pat. Nos. 6,508,859 and 7,141,097.

U.S. Pat. No. 9,533,109 describes a bubble entrapment device, wherein the outlet port extends into the chamber and the bubble trap comprises several chambers arranged in a series. Such a device works on the simple principle that bubbles rise to the top of the device and the assumption that, air does not enter the outlet port that extends into the chamber unless the chamber is half full of air. This assumption is incorrect as bubbles may still enter the outlet port, as the bubbles move towards the top of the device. The device further provides a plunger for insertion into the bubble trap for switching between a venting mode, in which bubbles move freely through the outlet, and an in-use mode. Switching between modes is achieved by rotating the plunger. In the bubble trap of U.S. Pat. No. 6,537,356 purging of air is achieved by temporarily reversing the fluid flow.

U.S. Pat. No. 6,537,356 describes a peanut-shaped chamber for trapping gas and solids in a fluid stream wherein an outlet nozzle projects into the chamber. One disadvantage of such a bubble trap is that depending on external factors it is still possible for bubbles to enter the outlet nozzle that projects into the chamber. The bubble trap described aims to overcome the possibility of bubbles entering the outlet nozzle by restricting the size of the lumen of the outlet nozzle to try and prevent larger bubbles from escaping into the patient bloodstream.

Another disadvantage of a narrowed outlet nozzle, as described in U.S. Pat. No. 6,537,356 is that it does not prevent the intake of bubbles into the outlet nozzle, as is described in the patent application. Larger gas bubbles will simply deform to fit the narrower lumen while smaller bubbles will pass right through. The net result is that the patient is still subjected to an elevated overall volume of gas along with the associated increased risk of large gas bubbles forming in the vasculature, causing damage to the blood vessel lumen and blockage of the blood vessel fluid flow such that oxygenation is reduced.

A further disadvantage of a narrowed outlet nozzle, as described in U.S. Pat. No. 6,537,356, is that the narrow outlet may become air-locked more readily, stopping or restricting the flow within the outlet nozzle. As such there would likely be an increased need for monitoring of the tubing and regular agitation to break up the bubbles sufficiently, so as to free up the flow through the outlet nozzle.

A further disadvantage of a narrowed outlet nozzle, as described in U.S. Pat. No. 6,537,356, is that reducing the outlet nozzle would restrict the flow of fluid exiting the degassing chamber and altering the dosing regimen of medication received by the patient. This is of particular issue with certain medications with a narrow therapeutic window, wherein the smallest deviation in the dosing regimen could become toxic to the patient.

The bubble trap of U.S. Pat. No. 6,537,356 is described as intended to be disposable, and as such is not suitable for repeated or continuous use. The user would therefore need to keep watch and move the device into another position to prolong its one-time usage time, as too long in one position would result in the centrally located tube no longer being submerged in the fluid, leading to air entering the outlet nozzle and into the blood stream of a patient.

A further disadvantage of the bubble trap as described in U.S. Pat. No. 6,537,356 is that air present in the device before use may not be readily flushed from the device prior to use, meaning that the device will not work as efficiently nor for a long duration limiting its operational capacity.

U.S. Pat. No. 5,674,199 describes a bubble trap suitable for blood transfusion devices, where an extracorporeal circuit is formed. In this bubble trap the inlet tube extends into the chamber and a container that reverses the direction of blood flow introduced into the chamber. The effect of changing the direction of flow is that there is greater opportunity for bubbles in the blood to separate out from the blood before the blood exits through the exit port. The redirection of flow is said to also reduce stagnation and clotting of blood within the container.

A disadvantage of such a device is that it is not operational in a multitude of directions and is intended for use in a vertical orientation. In an IV drip set up, particularly where a bubble trap is positioned nearer to point of entry into the patient the bubble trap may be inverted due to movement of the patient. In the event that the device of U.S. Pat. No. 5,674,199 was inverted gas bubbles would readily move through the exit port as the air naturally travels upwards towards the exit port.

Another disadvantage of such a device is that sufficient fluid flow force is required to impart the change in direction of the fluid flow and prevent stagnation in the cup. This fluid flow force results in turbulence, friction and impact of the blood cells against the sides of the cup leading to haemolysis and poor-quality blood.

A further disadvantage of this cup design is that a proportion of blood still remains in the cup and as a result is unable to be utilised in transfusions.

Furthermore, while the device is suitable for removing bubbles from blood in an extracorporeal circuit, it is to be appreciated that this does not immediately render the device suitable for other purposes where fluid flow conditions are quite different, such as in an IV drip set-up.

There remains a need for improved bubble traps for the removal of gas bubbles degassed from a solution.

It is a goal of the present invention to provide an apparatus and/or method that overcomes at least one of the above-mentioned problems.

SUMMARY OF THE INVENTION

The present invention is directed to an apparatus suitable for separating and collecting gas bubbles entrained in a fluid, wherein the apparatus comprises a housing defining at least one chamber, the chamber having an inlet port and an outlet port; a diverter, namely a first diverter, positioned between the inlet port and the outlet port; and, an elongated exit tube with an intake end and an export end; wherein the intake end of the elongated exit tube is centrally located within the chamber and the export end of the elongated exit tube is connected to the outlet port of the chamber.

In use, fluid (i.e. a combination of a liquid and a gas) generally flows through the inlet port 204 and into the chamber 302 of the apparatus 200 under the influence of a pressure gradient (i.e. high pressure to low pressure), induced by a pump or any other means of inducing flow rate, when the apparatus forms part of an IV drip set-up or other system where an apparatus suitable for separating and collecting gas bubbles entrained in a fluid is required.

The advantage of providing the features of a diverter and an elongated exit tube in combination is that fluid is directed away from the intake end of the elongated exit tube thereby reducing the risk of air intake into the elongated exit tube.

The advantage of providing the features of a diverter and an elongated exit tube in combination is that that fluid is directed away from the intake end of the elongated exit tube regardless of the orientation of the device.

A further advantage of the apparatus of the present invention is that the design combining the features of a diverter and an elongated exit tube captures the build-up of gas within the chamber such that the number and frequency of pump alarms in the set-up, within which the present invention is intended to be used, is reduced, thereby lowering alarm alerts and subsequent alarm fatigue, a leading challenge among medical staff.

A further advantage of the apparatus of the present invention is the provision of a cost-effective solution, suitable for mass-production that can integrate seamlessly with existing line connector technology.

In a further embodiment, the chamber is a larger volume relative to the inlet tubing and outlet tubing.

The advantage of having a chamber having a larger volume relative to the inlet tubing and outlet tubing is that laminar flow is encouraged as the liquid expands to fill the chamber. In larger volumes a reduction in turbulence is observed.

In a further embodiment, the first diverter forms a solid shape.

In a further embodiment, the first diverter defines a compartment within the chamber, wherein the diverter comprises a base portion and a rim.

In a further embodiment, the base portion of the diverter is adjacent the inlet port.

In a further embodiment, the base portion of the diverter abuts the inlet port.

In a further embodiment, the rim of the diverter is adjacent the outlet port.

In a further embodiment, the intake end of the elongated exit tube is centrally located within the compartment formed by the diverter.

One advantage of locating the elongated exit tube centrally within the compartment formed by the diverter is to hold a volume of liquid, which is substantially free of bubbles, centrally within the chamber and in front of the intake end of the elongated exit tube.

Said volume of liquid tends to be less turbulent and slower moving than the fluid in other portions of the chamber. Another advantage is that slower moving volume of liquid results in a more laminar flow that is lower in friction (drag) having increased buoyant force meaning that any bubbles that do remain in the volume of liquid will more speedily move towards the uppermost outer portion of the chamber.

In a further embodiment, the rim of the diverter extends beyond the intake end of the elongated exit tube.

Bubbles tend to 'stick' to surfaces, such as the housing of the chamber, but can become dislodged, particularly when agitated or knocked. Where a bubble trap is to be positioned at the patient end of an IV drip set-up the issue of dislodging bubbles from the surfaces of the trap are elevated as the patient moves around.

One advantage of positioning the rim of the diverter beyond the intake end of the elongated exit tube is that any bubbles that do become dislodged will still be diverted away from the intake end of the elongated exit tube. The bubbles are prevented from commuting directly past the intake end of the elongated exit tube, thus reducing the possibility of bubbles entering the elongated exit tube, via the intake end, and traversing towards the patient and into the patient's bloodstream.

In a further embodiment, the diverter is formed of rounded contours.

Bubbles tend to break away from sharp edges. The advantage of providing the diverter with rounded contours is that bubbles tend to remain attached to the sides of the container. As such bubble detachment is controlled and the risk of bubbles breaking off and floating past the intake end of the elongated exit tube is reduced. While rounded contours are described, it is appreciated that other shapes may also be suitable.

In a further embodiment the apparatus comprises at least one internal surface, wherein a portion of the internal surface comprises a surface treatment.

In a further embodiment, the surface treatment is a chemical treatment. In another embodiment, the surface treatment is a mechanical treatment.

One advantage of the surface treatment is that bubble detachment is controlled.

In a preferred embodiment the at least one internal surface of the apparatus wherein a portion of the internal surface comprises a surface treatment is the diverter.

In a further embodiment, the surface treatment comprises at least one smooth surface.

Bubbles tend to stick to smooth surfaces. One advantage of at least one smooth surface is that bubbles tend to remain attached to the smooth surface.

In a further embodiment the surface treatment comprises at least one textured surface.

Bubbles tend to break away from rough and inhomogeneous surfaces. One advantage of at least one textured surface is that bubbles can break away to form a free-floating bubble in the liquid, which, under buoyancy, will then move towards the uppermost portion of the chamber.

Textured, rough and/or inhomogeneous surfaces comprise a plurality of dimples, within which attached bubbles may sit.

A further advantage of a textured surface treatment is that the diameter of the bubble is contained by the dimensions of the dimple within which the bubble sits. The size of each dimple limits the size of the bubble formed. Once a bubble becomes attached to a dimple of a textured surface it continues to grow as free-floating bubbles merge with the dimple-tethered bubble. Detachment of the bubble occurs once the size of the bubble exceeds a pre-determined size-limit up to which the dimple can retain hold of the bubble and beyond which the bubble will detach from the textured surface. Bubble detachment and bubble size is therefore controllable.

In a further embodiment the surface treatment comprises at least one smooth surface and at least one textured surface.

One advantage of combining at least one smooth and at least one textured surface is that the lodgement and dislodgement of gas bubbles can be controlled. In use, gas bubbles are encouraged to stick or release at certain positions of the diverter dependant on what surface treatment is used. The result being that bubbles are manipulated in such a way that they are either removed to the outer portion of the chamber or become stuck to a surface treatment such that the bubble is either directed away from or is prevented from flowing past the intake end of the elongated exit tube.

While surface treatments are described in context of the diverter, it is to be appreciated that surface treatments may also be applied to other surfaces of the apparatus such as the diffuser, the internal portion of the housing of the chamber and any other surfaces of the apparatus where control of bubble lodgement and dislodgement is desired.

In a further embodiment, there is an inflow tube with an intake end and an export end, the export end being centrally located within the chamber.

In a further embodiment, the inflow tube is a protrusion of the chamber walls about the inlet port.

In a further embodiment, the inflow tube comprises at least one male or female connector and the chamber wall comprises at least one male and female connector that corresponds to the at least one male or female connector of the inflow tube.

In a further embodiment, a portion of the inflow tube abuts a portion of the first diverter.

In a further embodiment, the portion of the inflow tube abuts the base portion of the first diverter.

In a further embodiment, the apparatus comprises a diffuser, wherein the diffuser comprises at least one hole.

In use, the bubbles, under fluid flow parameters, move through the at least one hole of said diffuser and into the chamber. The bubbles are then guided by the diverter towards the outer portions of the chamber and away from the intake end of the elongated exit tube. In this embodiment the at least one hole of said diffuser imparts an alternative direction of movement on the fluid entering the chamber, along with any gas bubbles entrained in the fluid.

The advantage of the diffuser is to slow the velocity of the fluid arriving from the inlet tube into the chamber.

In a further embodiment, the at least one hole is located on the uppermost portion of the diffuser.

In this embodiment the location of the at least one hole encourages gas bubbles to enter the chamber in a generally upward moving motion towards the uppermost outer portion of the chamber.

In a further embodiment, the diffuser comprises a plurality of holes. In a preferred embodiment the diffuser comprises 4 holes. In a most preferred embodiment each hole is about 0.25 mm in diameter.

One advantage of having a plurality of holes is the reduction in the occurrence of air-locking. As such fluid flow and fluid pressure entering the chamber is maintained.

A further advantage of having a plurality of holes is that, in the event the apparatus is moved altering the orientation, there remains at least one hole in a generally uppermost position on the diffuser. As such gas bubbles entering the chamber are still enabled to move in a generally upwards motion towards the uppermost outer portions of the chamber.

A further advantage of having a plurality of holes is that sticking, or attachment of bubbles is limited.

In a further embodiment, the diffuser is positioned between the inlet port and the outlet port. In a further embodiment, the diffuser is positioned between the inlet port and the first diverter. In a further embodiment, the diffuser is positioned at the export end of the inflow tube. In a further embodiment, the diffuser is positioned at any point along the length of the inflow tube.

In a further embodiment, the diffuser is formed of the inflow tube.

In a further embodiment, the inflow tube of the diffuser is elongated.

One advantage to extending the length of the inflow tube is to improve structural stability where a plurality of holes is present.

In a further embodiment, the inflow tube forms a plurality of inflow tubes, wherein each inflow tube extends radially towards the outer portions of the chamber.

An advantage to having a plurality of inflow tubes is that the path of the bubble is further directed towards the outer and uppermost portion of the chamber.

In another embodiment the plurality of holes of the diffuser are smaller relative to the size of the bubbles arriving at the diffuser from the inlet port. In use, the larger bubbles are forced, under fluid flow parameters, through the plurality of small holes of said diffuser, such that the larger bubble arriving at the diffuser becomes a plurality of smaller bubbles once it has passed through the plurality of small holes of said diffuser. The plurality of smaller bubbles present in the chamber is then guided towards the outer portions of the chamber by the first diverter.

One advantage of the diffuser comprising a plurality of smaller holes relative to the size of the bubbles arriving at the diffuser from the inlet port is that larger bubbles entrained in the incoming fluid are broken up, by the diffuser, into several smaller bubbles prior to entering the chamber. These smaller bubbles are of optimal size having less surface area subjected to drag and as such travel faster through the liquid. The optimal bubble size is determined by flow rate, bubble size and other environmental conditions, but an optimal bubble is one that exhibits optimal buoyancy characteristics, i.e. that the bubble is not restricted by turbulence, drag, friction, collisions, coalescence and other limiting factors, as well as having a volume of gas sufficient to overcome the liquid retention properties enabling them to travel much more quickly to the outer portions of the chamber and thus are more quickly diverted away from the intake end of the elongated exit tube.

Cavities are bubbles that are from about 1 nm to 10 nm in diameter. Nanobubbles, or ultrafine bubbles, range from about 10 nm to 200 nm in diameter and have a typical transit time of about 0.1 cm/sec. As such nanobubbles have lower buoyancy and remain suspended in liquids for an extended period, due to Brownian Motion. Bubbles, whose diameters lie between 200 nm and 10 μm, are known as 'micro-nanobubbles' (MNBs). Microbubbles range from about 10 μm to 50 μm in diameter and tend to collapse in a liquid and disappear before reaching the surface or form a nanobubble and remain suspended. Ordinary bubbles, or macrobubbles, have a diameter ranging from about 100 μm to 1 mm and have a typical transit time of about 25 cm/sec. As such ordinary bubbles quickly rise to the surface of a liquid and collapse.

Another advantage of the diffuser is that the resulting smaller bubbles have a reduced overall volume of gas per bubble. Particularly small bubbles can remain suspended in the liquid. These particularly smaller gas bubbles are thought to be more readily absorbed by the body. In the unlikely event that a bubble should find its way out of the chamber via the exit tube and into the circulatory system of a patient using the apparatus the associated risks of air present in the vasculature is greatly reduced.

In another embodiment the apparatus comprises a second diverter.

In a further embodiment the second diverter is positioned between the first diverter and the intake end of the elongated exit tube.

In a further embodiment the second diverter is formed of a container with a base portion and a rim.

In a preferred embodiment the base portion of the second diverter abuts the intake end of the elongated exit tube.

One advantage of a second diverter is that fluid flow with entrained gas is diverted away from the intake end of the elongated exit tube. Where the apparatus is inverted this is particularly useful in maintaining the collected gas at a position away from the intake end of the elongated exit tube.

In another embodiment, the apparatus comprises an occluder suitable for blocking the intake end of the elongated exit tube.

As the collected gas increases the level of the liquid contained in the chamber of the apparatus drops, such that collected gas may escape through the intake end of the elongated exit tube if the level of the liquid contained in the chamber of the apparatus drops beyond a certain point. In use, the occluder floats in the volume of liquid contained in the chamber of the apparatus, as the liquid level drops the occluder abuts the intake end of the elongated exit tube such that gas is prevented from exiting the chamber into the elongated exit tube.

In a further embodiment, the occluder is located in the elongated exit tube.

In a further embodiment, the apparatus comprises at least one venting port.

The advantage of providing a venting port is that the bubbles trapped in the device can be easily removed at any time prior to or during use, meaning that the bubble trap can continue to be used with minimum impact on the functioning of the infusion of fluids into a patient.

Another advantage of a venting port is that a low-pressure gradient can be created to encourage liquid to rapidly fill the chamber, while preventing air/fluid flow through the exit tube in the direction of the patient.

A further advantage of a venting port is that priming of the bubble trap apparatus is enabled, allowing any air present in the chamber of the apparatus to be expelled from the chamber prior to use.

A further advantage of a venting port is that by enabling removal of any bubbles or air present in the device improves the efficiency and effectiveness of the device.

A further advantage of a venting port is that it renders the apparatus suitable for continuous use. An apparatus without a venting port would slowly fill with gas overtime, meaning that it is only suitable as a disposable item that would need regular replacement to avoid the associate risks of air present in the vasculature.

In another embodiment the apparatus comprises a selectively permeable membrane.

In a further embodiment the selectively permeable membrane comprises a gas impermeable-liquid permeable membrane.

In a further embodiment the gas impermeable-liquid permeable membrane is located at the intake end of the elongated exit tube.

In use, liquid in the chamber can exit from the chamber through the gas impermeable-liquid permeable membrane into the elongated exit tube, while the gas bubbles remain in the chamber.

In a further embodiment the selectively permeable membrane comprises a gas permeable-liquid impermeable membrane.

In a further embodiment the gas permeable-liquid impermeable membrane is positioned at the venting port.

In use, the gas bubbles collected in the chamber may pass through the gas permeable membrane of the venting port, while liquid in the chamber is prevented from exiting the chamber via the venting port.

One advantage of a gas permeable-liquid impermeable membrane is that no release means is needed and as such no monitoring or toggling of said release means is necessary. Gas is automatically purged from the chamber without the need for additional action or automation.

Another advantage of the gas permeable-liquid impermeable located between the chamber and the venting port is that liquid in the chamber is prevented from exiting the chamber through the venting port, thus minimising lost fluids, reducing waste and cost of use.

In another embodiment, the apparatus comprises a filter membrane positioned between the inlet port and the exit port.

Bacteria and solid particulate material can find their way into liquids to be administered to a patient. Examples of particulate materials include for example glass particles from opening glass ampoules, particles from rubber stoppers or conglomerates of the parenteral nutrition components, drug incompatibility reactions, incomplete reconstitution during preparation of liquid solutions and other drug formulation issues. Bacterial and particulate contamination of the liquid solutions for delivery to the patient can result in patient care complications if such contaminations end up in the blood stream of the patient.

An advantage of a filter membrane is to capture bacteria and particulates and prevent them from exiting the chamber of the apparatus into the elongated exit tube and therefore to prevent them from entering the patient blood stream.

In another embodiment, the filter membrane abuts the intake end of the elongated exit tube.

In another embodiment the venting port is coupled with a release means, suitable for purging trapped gas bubbles from the apparatus on moving the release means from a closed position to an open position; Such that, in use, when the release means is in the open position the trapped gas is purged from the chamber of the apparatus through the venting port.

The advantage of coupling the vent to a release means is that the expulsion of the gas bubbles can be controlled, and loss of fluids intended for infusion is minimised.

In another embodiment the release means comprises a pushing action. In another embodiment the release means comprises a pulling action. In another embodiment the release means comprises a rotating action. In another embodiment the release means comprises sliding action.

In use, when one or more action is performed on said release means the entrained gas is released from the chamber of the apparatus via the venting port.

In a further embodiment, the release means is automated.

An advantage of automating the release means, and thus the purging of air from within the bubble trap, is that reduced monitoring of the trap is required by hospital staff, freeing up their time to be spent on other important duties.

In a further embodiment, the apparatus comprises a sensor, suitable for monitoring the gas level within the chamber of the apparatus.

An advantage of a sensor is to detect the entry of gas bubbles into the chamber of the apparatus and measure the amount of gas present to a pre-determined acceptable level.

In a further embodiment the apparatus comprises an alerting means.

One advantage of an alerting means is to indicate that the amount of gas present in the chamber has exceeded the pre-determined acceptable level so that venting is initiated.

Another advantage of an alerting means is to indicate when the release means is be operated and the venting port to be opened, such as to expel collected gas from the chamber and maintain optimal operation of the apparatus.

In a further embodiment, the chamber is spherical. In a further embodiment, the chamber is square. In a further embodiment, the chamber is oblong. In a further embodiment, the chamber is triangular.

The advantage of the device being spherical is that it enables the trapped gas to collect away from the elongated exit tube in any orientation.

In a further embodiment, the chamber is opaque. In a further embodiment, the chamber is translucent. In a further embodiment, the chamber is transparent.

One advantage of the chamber being transparent is that fluids and gas formation can be easily observed and monitored.

In another embodiment the apparatus comprises a measurement system. In use the measurement system takes a reading of the amount or level of trapped air or collected gas bubbles in the chamber.

In a preferred embodiment the measuring system is a gradient rule.

One advantage of a measurement system is that the volume of gas present in the chamber of the apparatus may be accurately measured.

In another embodiment the apparatus comprises a display. In use, the display provides a readable indication of the measurement taken pertaining the amount or level of trapped air or collected gas bubbles in the chamber.

One advantage of a display is the clear communication of the volume of gas present in the chamber of the apparatus.

The size and dimensions of the apparatus may be modified depending on the set-ups with which it is required to be used. For example, the size and dimensions of the apparatus could be reduced for use in blood transfusion set-ups. An advantage of a reduced size bubble trap is a minimisation of fluid loss in the apparatus.

In another embodiment the apparatus comprises an injection port. In use the injection port allows an operator to administer a bolus injection. This is useful where a particularly high dosage of a medicine is required.

In a preferred embodiment the injection port is positioned between the outlet port of the apparatus and the point of entry via a cannula in the direction of the patient.

The advantage of the injection port being positioned between the exit port of the apparatus and the point of entry via a cannula in the direction of the patient is that a reliable concentration of medication is administered.

Another advantage of the injection port being positioned between the exit port of the apparatus and the point of entry via a cannula in the direction of the patient is that the whole bolus injection is ensured as entering the patient blood stream.

In another embodiment the operator is automated.

In another embodiment the apparatus comprises a locking mechanism having an open position and a closed position.

In a further embodiment the locking mechanism is positioned adjacent the inlet port. In use, when the locking mechanism is in an open position, liquid and any entrained gas flows into the chamber of the apparatus. When the locking mechanism is in a closed position, liquid and any entrained gas is prevented from leaving the chamber of the apparatus.

In a further embodiment the apparatus comprises a plurality of locking mechanisms, wherein the position of each locking mechanism is determined independent of one another.

One advantage to a locking mechanism or combination of lacking mechanisms is that fluid flow may be readily controlled, with flow from or in one direction being capable of being arrested or enabled to continue flowing as needed.

In a further embodiment the locking mechanism is positioned adjacent the outlet port. In use, when the locking mechanism is in an open position liquid and any entrained gas within the chamber of the apparatus may exit the chamber through the elongated exit tube and into the outlet tubing in the direction of the patient. When the locking mechanism is in a closed position liquid and any entrained gas is prevented from entering the chamber of the apparatus.

In another embodiment the apparatus is formed of a rigid material.

In another embodiment the apparatus is formed of malleable material. In a preferred embodiment the malleable material is a polymer.

In another embodiment the apparatus is formed of individual component parts. Component parts would require construction to form the complete apparatus prior to use.

In another embodiment the apparatus is capable of being manufactured as a single piece unit.

In another embodiment the apparatus is manufactured by means of 3D-printing. In another embodiment the apparatus is manufactured by means of injection moulding.

In another embodiment, the apparatus as hereinbefore described comprises a foot.

In another embodiment, the foot comprises a clamping device, the clamping device being operable to fixedly attach the apparatus to a surface.

In use, attachment of the apparatus to a surface by operating the clamping device of the foot provides secures the apparatus into a fixed position, providing stability.

In another embodiment, the surface is selected from clothing, bed sheets, IV pole or other nearby structure.

In another aspect of the invention there is provided an apparatus comprising a housing defining at least one chamber, the chamber having an inlet port, an outlet port and a diffuser positioned between the inlet port and the outlet port, wherein the diffuser comprises at least one hole.

In use, the bubbles, under fluid flow parameters, move through the at least one hole of said diffuser and into the chamber. In this embodiment the at least one hole of said diffuser imparts an alternative direction of movement on the fluid entering the chamber, the fluid comprised of liquid and gas bubbles entrained in the liquid.

The advantage of the diffuser is to slow the velocity of the fluid arriving from the inlet tube into the chamber of the apparatus.

In a further embodiment, the at least one hole is located on the uppermost portion of the diffuser.

In this embodiment the location of the at least one hole encourages gas bubbles to enter the chamber in a generally upward moving motion towards the uppermost outer portion of the chamber.

In a further embodiment, the diffuser comprises a plurality of holes.

One advantage of having a plurality of holes is the reduction in the occurrence of air-locking. As such fluid flow and fluid pressure entering the chamber is maintained.

In another embodiment the diffuser comprises a plurality of holes, wherein the holes are spaced apart and positioned in a generally radial arrangement about a circumference of the diffuser.

An advantage of having a plurality of holes spaced apart and positioned in a generally radial arrangement is that, in the event the apparatus is moved altering the orientation, there remains at least one hole in a generally uppermost position on the diffuser. As such gas bubbles entering the chamber are still enabled to move in a generally upwards motion towards the uppermost outer portions of the chamber.

In a further embodiment, the diffuser is formed of an inflow tube, the inflow tube positioned about the inlet port.

In a further embodiment, the inflow tube of he diffuser is elongated.

One advantage to extending the length of the inflow tube is to improve structural stability where a plurality of holes is present.

In a further embodiment, the inflow tube forms a plurality of inflow tubes, wherein each inflow tube extends radially towards the outer portions of the chamber.

In another embodiment the plurality of holes of the diffuser are smaller relative to the size of the bubbles arriving at the diffuser from the inlet port. In use, the larger bubbles are forced, under fluid flow parameters, through the plurality of small holes of said diffuser, such that the larger bubble arriving at the diffuser becomes a plurality of smaller bubbles once it has passed through the plurality of small holes of said diffuser. The plurality of smaller bubbles present in the chamber is then guided towards the outer portions of the chamber by the first diverter.

One advantage of the diffuser comprising a plurality of smaller holes relative to the size of the bubbles arriving at the diffuser from the inlet port is that larger bubbles entrained in the incoming fluid are broken up, by the diffuser, into several smaller bubbles prior to entering the chamber. These smaller bubbles are of optimal size having less surface area subjected to drag and as such travel faster through the liquid, meaning that they exhibit optimal buoyancy characteristics that enable them to travel much more quickly to the outer portions of the chamber and thus are more quickly diverted away from the intake end of the elongated exit tube.

Another advantage of the diffuser is that the resulting smaller bubbles have a reduced the overall volume of gas per bubble. Particularly small bubbles can remain suspended in the liquid. These particularly smaller gas bubbles are thought to be more readily absorbed by the body. In the unlikely event that a bubble should find its way out of the chamber via the exit tube and into the circulatory system of a patient using the apparatus the associated risks of air present in the vasculature is greatly reduced.

In another embodiment, the apparatus is suitable for separating and collecting gas bubbles entrained in a fluid.

In another aspect of the invention there is provided an apparatus comprising a housing defining at least one chamber, the chamber having an inlet port and an outlet port, wherein the chamber comprises at least one surface, wherein a portion of the at least one surface of the chamber comprises a surface treatment suitable for control of a bubble and its movement within the chamber.

In use, when a bubble come into contact with the portion of the at least one surface of the chamber comprising the surface treatment the bubble attaches to, or dislodges from, said portion of the surface of the chamber comprises the surface treatment.

In another embodiment the surface treatment encourages the attachment of the bubble to the portion of the internal surface comprising the surface treatment.

In another embodiment the surface treatment encourages the dislodgement of the bubble from the portion of the internal surface comprising the surface treatment. Such that, in use, the bubble becomes a free-floating bubble within a volume fluid present within the chamber.

In another embodiment the at least one internal surface is a diverter.

In another aspect of the invention there is provided an apparatus comprising a housing defining at least one chamber, the chamber having an inlet port, an outlet port and a selectively permeable membrane.

In a further embodiment the selectively permeable membrane comprises a gas impermeable-liquid permeable membrane.

In a further embodiment the selectively permeable membrane comprises a gas permeable-liquid impermeable membrane.

In a further embodiment the gas impermeable-liquid permeable membrane is located at the outlet port.

In use, liquid in the chamber can exit from the chamber through the gas impermeable-liquid permeable membrane, while the gas bubbles remain in the chamber of the apparatus.

In a further embodiment, the apparatus comprises a venting port.

In a further embodiment, the gas permeable-liquid impermeable membrane is positioned at the venting port.

In use, the gas bubbles collected in the chamber may pass through the gas permeable-liquid impermeable membrane of the venting port, while liquid in the chamber is prevented from exiting the chamber via the venting port.

One advantage of a gas permeable-liquid impermeable membrane is that no release means is needed an as such no monitoring or toggling of said release means is necessary. Gas is automatically purged from the chamber without the need for additional action or automation.

Another advantage of the gas permeable-liquid impermeable located between the chamber and the venting port is that liquid in the chamber is prevented from exiting the chamber through the venting port, thus minimising lost fluids, reducing waste and cost of use.

In another embodiment, the apparatus is suitable for separating and collecting gas bubbles entrained in a fluid In another embodiment, the apparatus is suitable for use in an IV drip set-up.

In another aspect of the invention there is provided an apparatus comprising a housing defining at least one chamber, the chamber having an inlet port, an outlet port and a filter.

In another embodiment, the filter membrane is positioned between the inlet port and the exit port.

Bacteria and solid particulate material can find their way into liquids to be administered to a patient. Examples of particulate materials include for example glass particles from opening glass ampoules, particles from rubber stoppers or conglomerates of the parenteral nutrition components, drug incompatibility reactions, incomplete reconstitution during preparation of liquid solutions and other drug formulation issues. Bacterial and particulate contamination of the liquid solutions for delivery to the patient can result in patient care complications if such contaminations end up in the blood stream of the patient.

An advantage of a filter membrane is to capture bacteria and particulates and prevent them from exiting the chamber of the apparatus and to therefore prevent them from entering a patient blood stream.

In another embodiment, the filter membrane abuts the outlet port.

In another embodiment, the apparatus is suitable for separating and collecting gas bubbles entrained in a fluid.

In another embodiment, the apparatus is suitable for use in an IV drip set-up.

In another aspect of the invention there is provided an apparatus as hereinbefore described wherein the apparatus is arranged in a circuit.

A blood transfusion set-up would typically be arranged in a circuit. It is to be appreciated that while the bubble trap as hereinbefore described, has been described in context of an IV drip, which generally does not form a circuit, it may be adapted for use in a blood transfusion set-up.

In another aspect of the invention there is provided an apparatus as hereinbefore described wherein the apparatus comprises a plurality of chambers arranged in a series.

The advantage of providing a plurality of chambers arranged in a series, is that bubble trapping and removal can be repeated several times, meaning that the risk of a bubble entering the patient's blood stream is further reduced.

In a further embodiment, each of the plurality of chambers is connectable to one another by means of interconnecting tubing.

In another aspect of the invention there is provided an intravenous line kit wherein the kit comprises at least one intravenous drip bag; at least one drip chamber; at least one supply tube having a proximal end and a distal end; a bubble trap; a flow control means; at least one clamp; and, a cannula; wherein the bubble trap comprises a diverter.

In a further embodiment, the bubble trap comprises the apparatus of the present invention as hereinbefore described.

The apparatus of the present invention may be suitable for use within an IV drip set up. The apparatus may be incorporated at any point along the length of the primary IV tubing, secondary tubing or extension tubing.

In a further embodiment the preferred position for the apparatus of the present invention is directly before the cannula in an IV drip set-up.

In another embodiment the position for the apparatus of the present invention is before a bubble monitoring device, such as an IV pump alarm system.

In another aspect of the invention there is provided an intravenous line kit wherein the kit comprises at least one intravenous drip bag; at least one drip chamber; at least one supply tube having a proximal end and a distal end; a bubble trap; a flow control means; at least one clamp; and, a cannula; wherein the bubble trap comprises a diffuser.

BRIEF DESCRIPTION OF THE DRAWINGS

The invention will be more clearly understood from the following description of some embodiments thereof, given by way of example only, with reference to the accompanying drawings, in which.

DETAILED DESCRIPTION OF PREFERRED EMBODIMENTS

Figure 1:
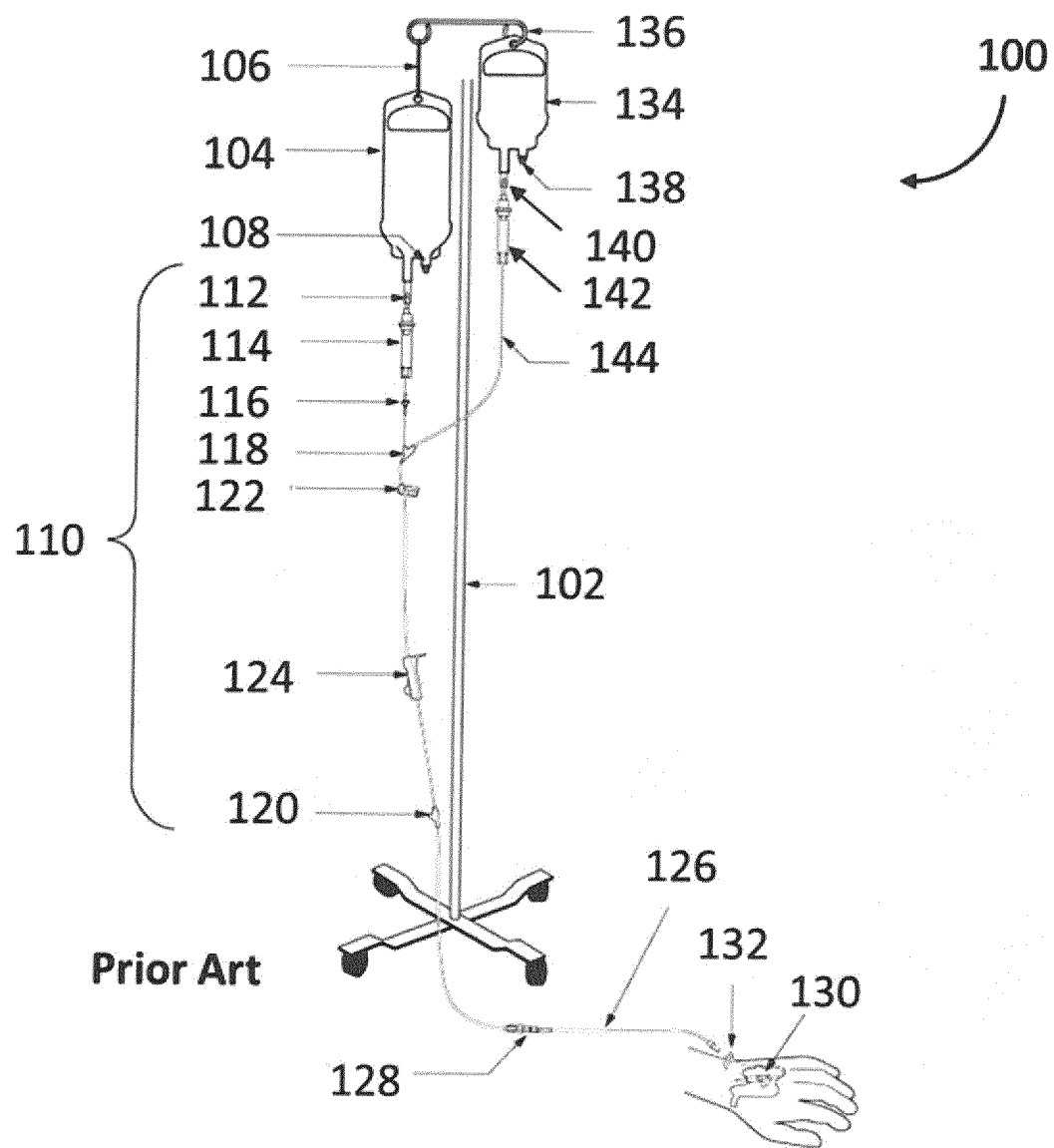
FIG. 1 is a diagrammatic representation of a typical IV drip set-up.
Figure 2:
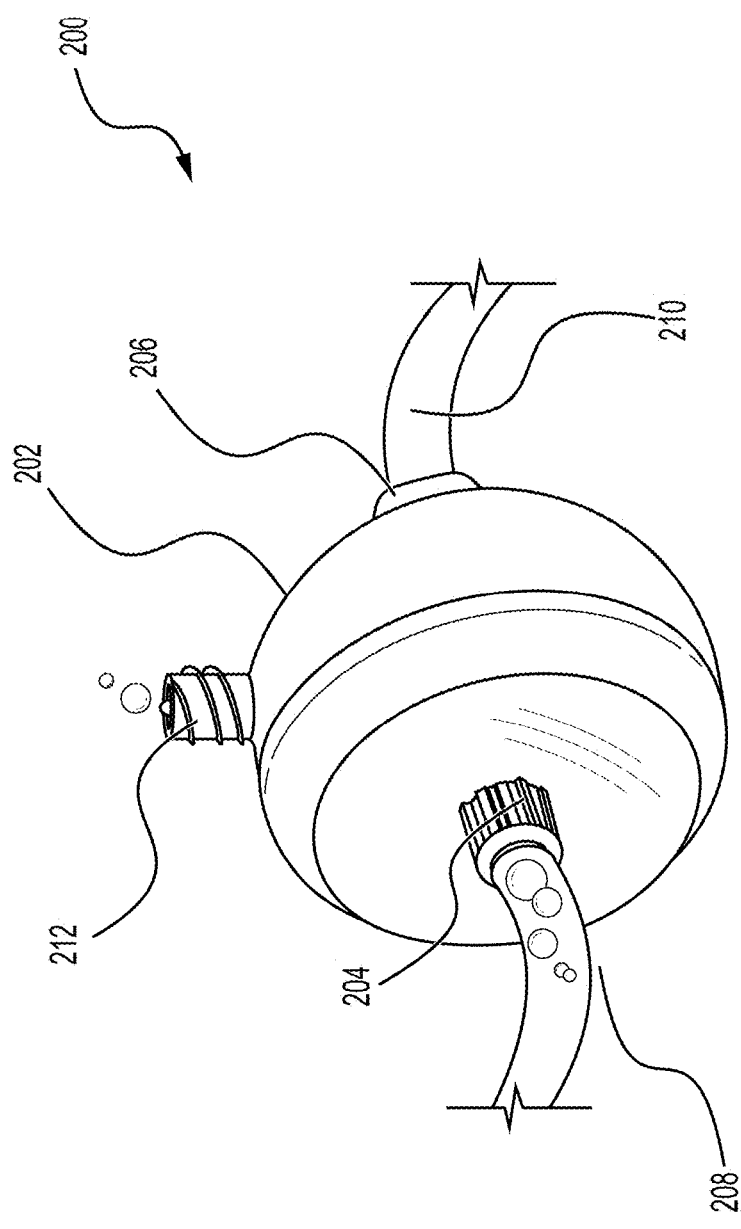
FIG. 2 is a 3D rendered external front-on view of an apparatus according to the present invention.

Referring to FIG. 2, there is provided an apparatus according to one embodiment of the present invention, indicated generally by reference numeral 200. The apparatus 200 comprises a housing 202, an inlet port 204 and an outlet port 206. Inlet tubing 208 is shown to be connected to the inlet port 204 and outlet tubing 210 is shown to be connected to the outlet port 206. In this embodiment a venting port 212 is shown.

Fluid comprising gas bubbles travels along the inlet tubing 208 and through the inlet port 204 into the apparatus 200. The bubbles entrained in the fluid then rise to the top outermost portion of the device. In this embodiment the trapped air may then be expelled from the system via the venting port 212. Fluid, substantially free from bubbles, exits the apparatus 200 via the outlet port 206 and moves along the outlet tubing 210 away from the apparatus 200.

While a venting port 212 is present in this embodiment it is to be appreciated that such a feature is not essential for the purpose of separating and collecting gas bubbles entrained in a fluid. Presence of a venting port 212 is a preferred feature but an apparatus 200 of the present invention may operate without it for a period of time. As such it is not intended that the invention be limited to the inclusion of a venting port 212.

While inlet tubing 208 and outlet tubing 210 is shown, in this embodiment such tubing is not necessarily an integral part of the apparatus 200 per se but refers to typical tubing that may be found in an IV drip set-up or similar, thus provides context as to how the apparatus 200 may be used. While the inlet tubing 208 and outlet tubing 210 are described as not being part of the apparatus 200, it is to be appreciated that in alternative embodiments the inlet tubing 208 and outlet tubing 210 is integrated into the apparatus, forming part of the apparatus 200 as a whole.

Figure 3:
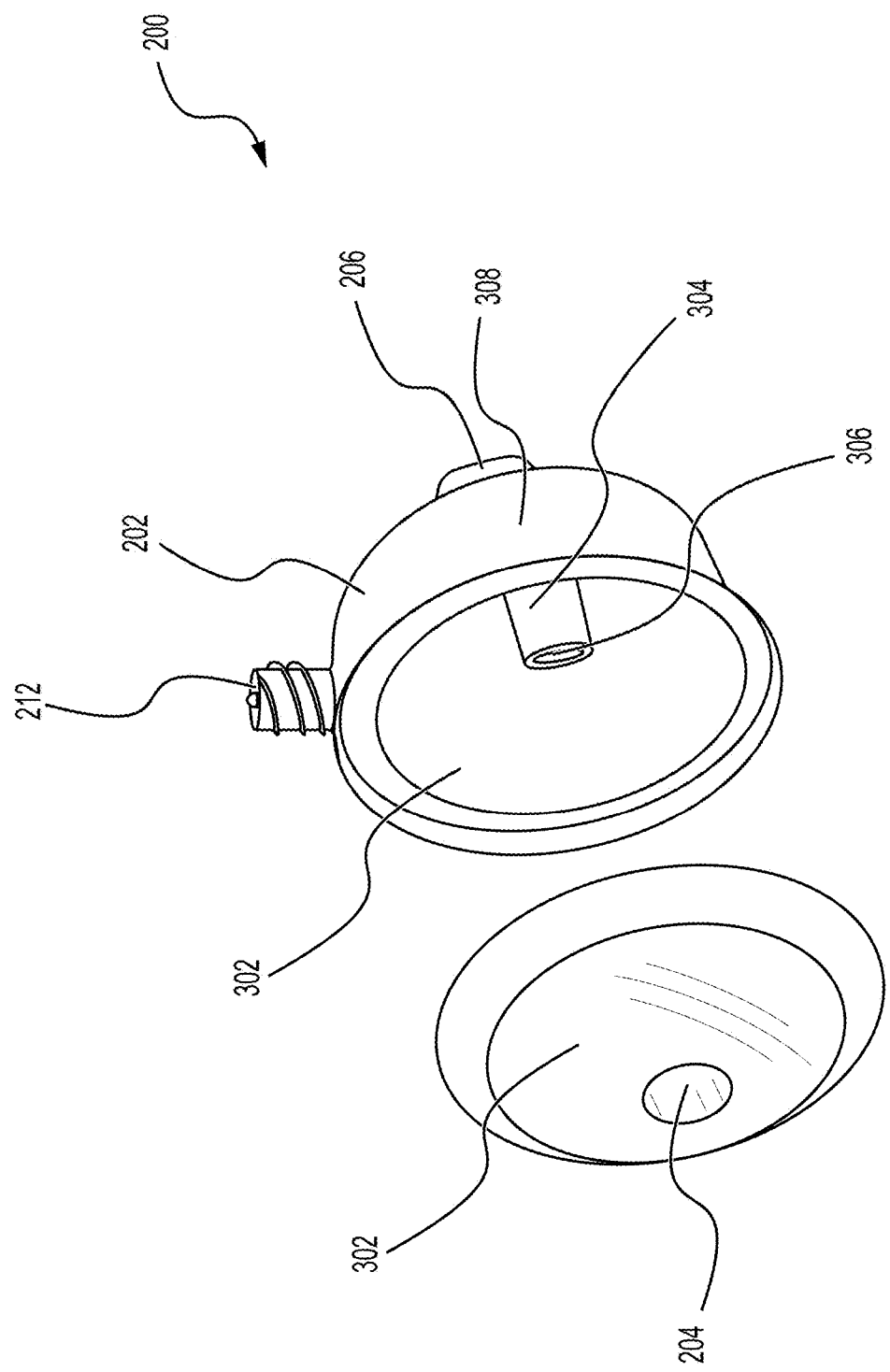
FIG. 3 is an exploded 3D rendered view of an apparatus according to the present invention.

Referring now to FIG. 3, an exploded perspective view of the apparatus is shown. Parts similar to features hereinbefore described are accorded the same reference number. The apparatus 200 comprises a housing 202 forming a chamber 302, with an inlet port 204 and an outlet port 206. The apparatus 200 also comprises an elongated exit tube 304, wherein the intake end 306 of the elongated exit tube 304 is centrally located within the chamber 302. The export end 308 of the elongated exit tube 304 is shown to be connected to the outlet port 206. In this embodiment a venting port 212 is also shown. As before, alternative embodiments may comprise an apparatus without a venting port 212.

Figure 4:
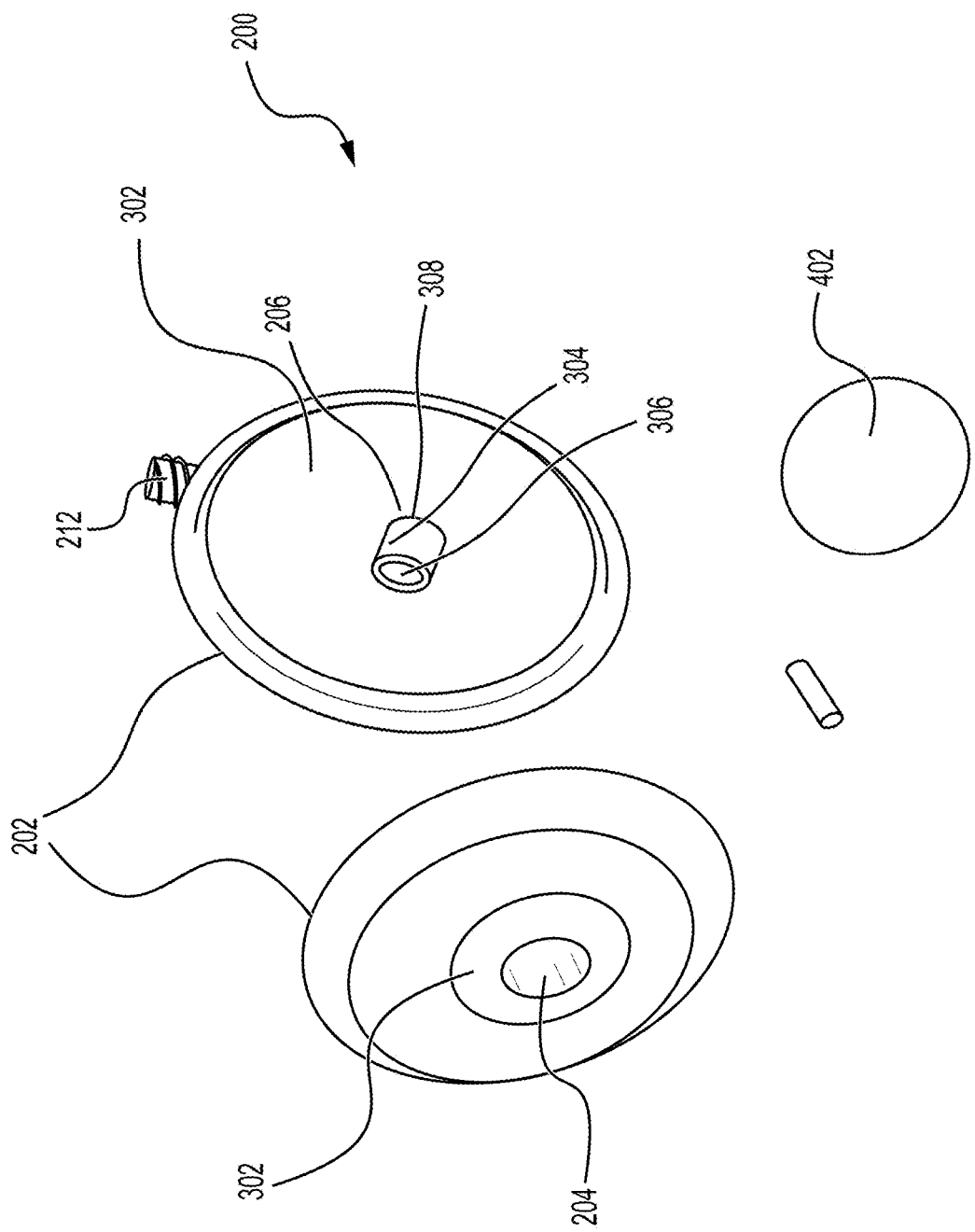
FIG. 4 is deconstructed view of the apparatus according to the present invention showing component parts thereof.

Referring now to FIG. 4, there is provided a deconstructed view of the component parts of the apparatus. Parts similar to features hereinbefore described are accorded the same reference number. The apparatus 200 comprises a housing 202 that, when constructed, forms a chamber 302. The apparatus 200 also comprises an inlet port 204, an outlet port 206, an elongated exit tube 304, wherein the elongated exit tube 304 has an intake end 306 and an export end 308 and a diverter 402. The intake end 306 of the elongated exit tube 304, when constructed, being centrally located within the chamber 302 with the export end 308 of the elongated exit tube 304 being connected to the outlet port 206.

Figure 5:
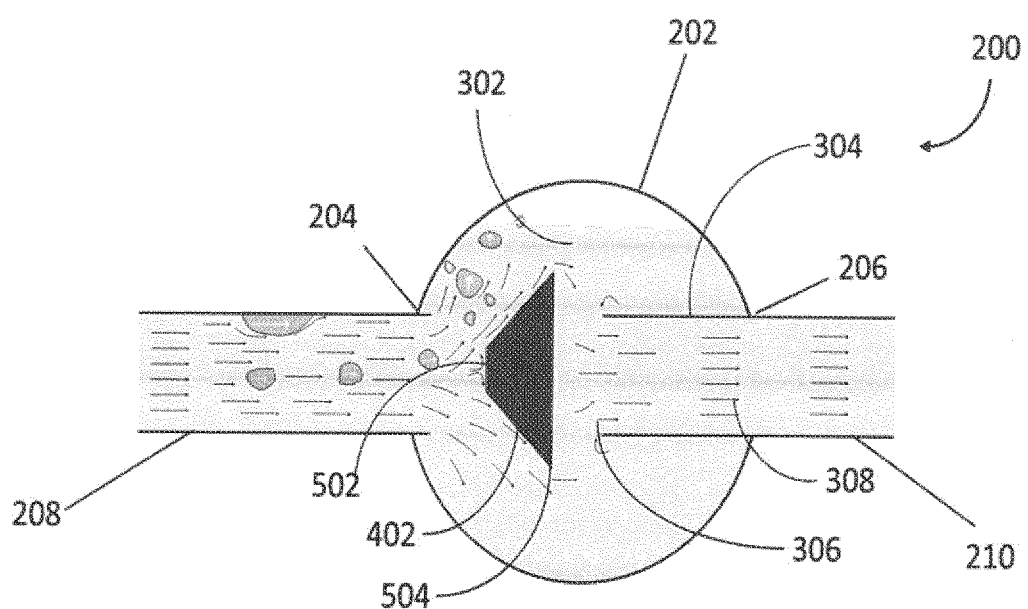
FIG. 5 is a diagrammatic view of an apparatus according to the present invention in use.

Referring now to FIG. 5, there is provided a diagrammatic view of the apparatus in use. Parts similar to features hereinbefore described are accorded the same reference number. The apparatus 200 comprises housing 202 that defines a chamber 302, an inlet port 204, an exit port 206 and an elongated exit tube 304 with an intake end 306 and an export end 308. In this embodiment, there is provided inlet tubing 208 connected to the inlet port 204 and outlet tubing 210 connected to the exit port 206. The diverter 402 is shown to comprise a base portion 502 and a rim 504. In this embodiment the diverter 402 and the inlet port 204 are spaced apart, such that the diverter 402 is suspended centrally within the chamber 302 of the apparatus 200. In this embodiment the diverter 402 and the intake end 306 of the elongated exit tube 304 are spaced apart, such that no part of the diverter 402 extends beyond the intake end 306 of the elongated exit tube 304.

In an alternative embodiment no inlet tubing 208 or outlet tubing 210 may be present.

In an alternative embodiment the diverter comprises at least one tether securing the diverter to the housing of the chamber, such that it is held in place.

In use, fluid arrives via the inlet port 204 into the chamber 302 of the apparatus 200. Bubbles are diverted, by the diverter 402, away from the elongated exit tube 304 and towards the outer portions of the chamber 302 of the apparatus 200. The fluid arriving into the chamber 302 has a first direction of fluid flow; on contact with the diverter 402 a different direction on fluid flow is imparted. The different direction of fluid flow generally follows the contours of the diverter 402, resulting in the fluid being pushed towards the outer portion of the chamber 302, along with any entrained gas therein. When the fluid arriving into the chamber 302 makes contact with the diverter 402, the fluid velocity is slowed. Slowing of the fluid velocity enables an elongated period of time within which bubbles may move away from the elongated exit tube 304 and towards the outer portions of the chamber 302 of the apparatus. Fluid, that is now substantially free from bubbles, collects between the diverter 402 and the intake end 306 of the elongated exit tube 304. The fluid substantially free from bubbles locates centrally within the chamber 302 and may be understood to be slower moving than fluid moving along the outer portions of the chamber 302. Fluid, substantially free from bubbles, exits the apparatus 200 via the outlet port 206 and moves along the outlet tubing 210 away from the apparatus 200.

Figure 6:
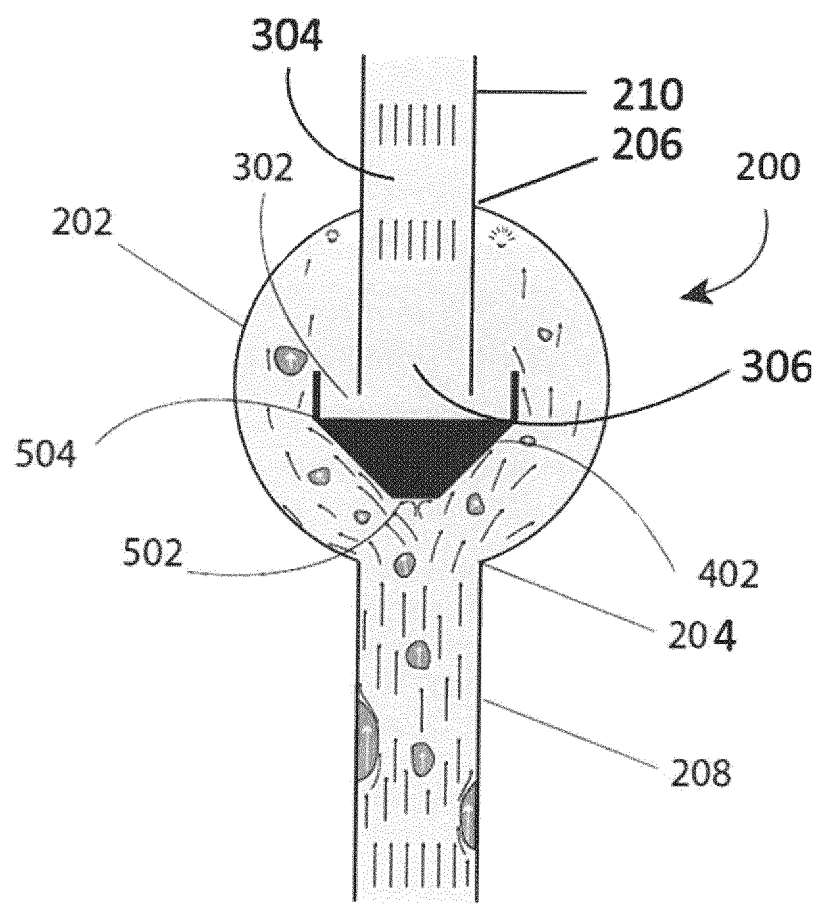
FIG. 6 is a diagrammatic view of an apparatus according to the present invention held in a vertical plane.

Referring now to FIG. 6 there is provided a diagrammatic view of the apparatus held vertically. Parts similar to features hereinbefore described are accorded the same reference number. The apparatus comprises a housing 202 forming a chamber 302 with an inlet port 204, inlet tubing 208 connected to the inlet port 204, a diverter 402, the diverter 402 having a base portion 502 and a rim 504, an elongated exit tube 304, wherein the intake end 306 of the elongated exit tube 304 is centrally located within the chamber 302 and outlet tubing 210 connected to the exit port 206. Fluid, substantially free from bubbles, exits the apparatus 200 via the outlet port 206 and moves along the outlet tubing 210 away from the apparatus 200.

In this embodiment the apparatus 200 is held in a substantially vertical plane, such that the inlet port 204 and the inlet tubing 208 are positioned at the lowermost portion of the apparatus 200.

In this embodiment the rim 504 of the diverter 402 extends beyond the intake end 306 of the elongated exit tube 304. Such a design would further ensure that bubbles remain directed away from the intake end 306 of the elongated exit tube 304.

In use, fluid and entrained gas travel upwards together through the inlet tubing 208 and arrives at the chamber 302 via the inlet port 204 positioned at the bottom of the chamber 302. As the fluid and entrained gas moves upwards through the chamber 302 it comes into contact with the diverter 402. The diverter 402 obstructs the first direction of flow of the fluid and entrained gas and causes a change in direction of the fluid and entrained gas, diverting it away from its original path (or first direction of flow) and towards the outer portions of the chamber 302. By obstructing the first direction of flow of the fluid and entrained gas the diverter 402 causes the fluid velocity to slow and thus the entrained gas bubbles also slow. This has the effect of causing a change to the external forces applied to the membrane of the gas bubble, such that buoyancy becomes the dominant force. As buoyancy becomes the dominant force the entrained gas bubbles move towards the uppermost outer portions of the chamber 302.

Figure 7:
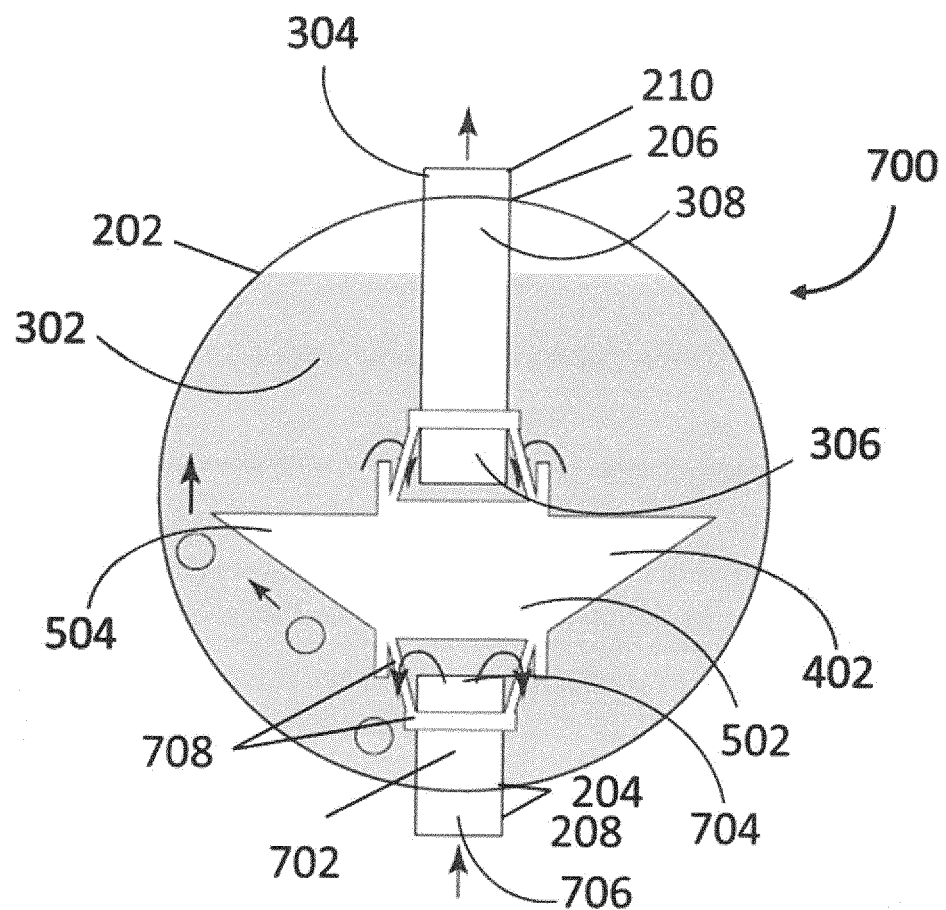
FIG. 7 is a diagrammatic view of an apparatus comprising a single diverter according to one embodiment of the present invention.

Referring now to FIG. 7, there is provided an apparatus according to another embodiment of the present invention. Parts similar to features hereinbefore described are accorded the same reference number. The apparatus 700 comprises a housing 202 forming a chamber 302, with an inlet port 204 and an outlet port 206, an inflow tube 702 with an export end 704 being centrally located within the chamber 302 and an intake end 706 of the inflow tube 702 being connected to the inlet port 204, an elongated exit tube 304 with the intake end 306 of the elongated exit tube 304 being centrally located within the chamber 302 and the export end 308 of the elongated exit tube 304 being connected to the outlet port 206, and a diverter 402, the diverter 402 having a base portion 502 and a rim 504.

In this embodiment, at least a portion of the base portion 502 of the diverter 402 is connected to the export end 704 of the inflow tube 702 by a tether 708 and at least a portion of the rim 504 of the diverter 402 is connected to the intake end 306 of the elongated exit tube 304 by a tether 708.

Figure 8:
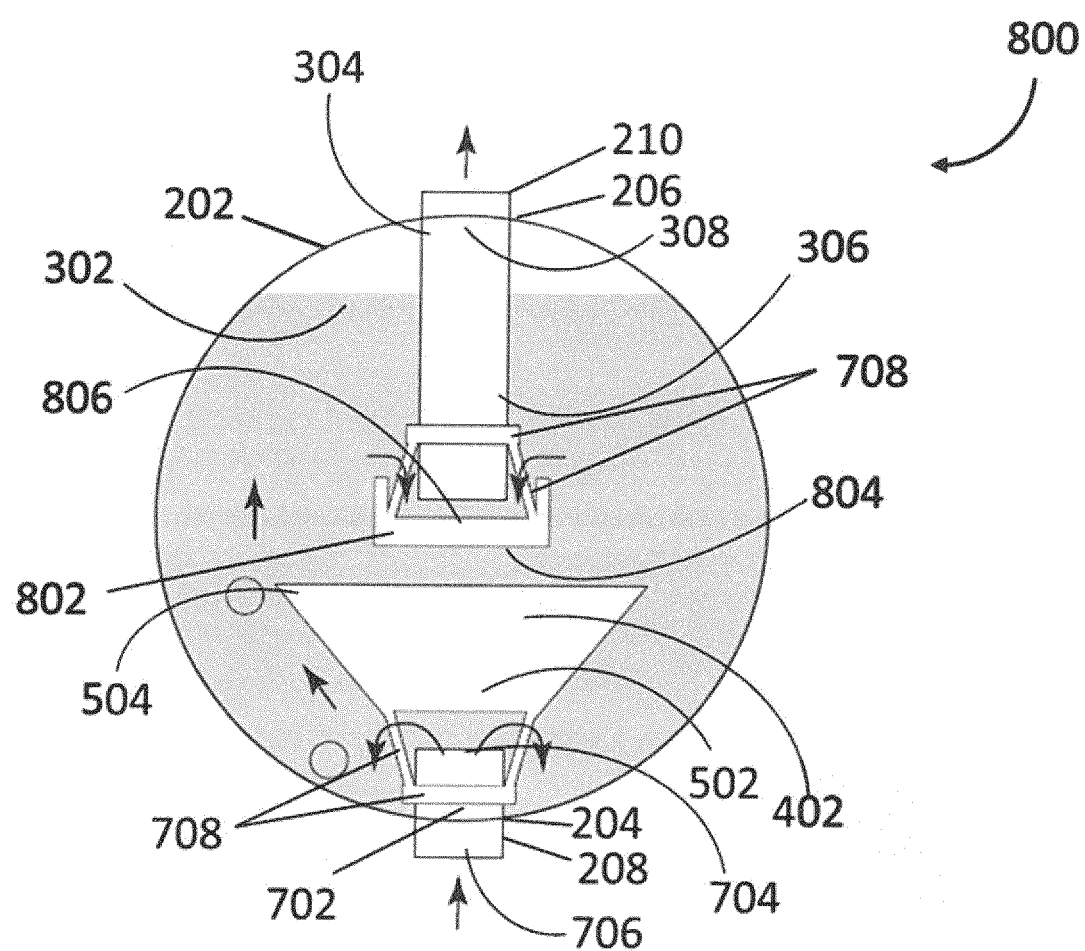
FIG. 8 is a diagrammatic view of an apparatus according to one embodiment of the present invention comprising a dual diverter.

Referring now to FIG. 8, there is provided an apparatus 800 according to another embodiment of the present invention comprising a dual diverter. Parts similar to features hereinbefore described are accorded the same reference number. The apparatus 800 comprises a housing 202 forming a chamber 302, with an inlet port 204 and an outlet port 206, an inflow tube 702 with an export end 704 being centrally located within the chamber 302 and an intake end 706 of the inflow tube 702 being connected to the inlet port 204, an elongated exit tube 304 with the intake end 306 of the elongated exit tube 304 being centrally located within the chamber 302 and the export end 308 of the elongated exit tube 304 being connected to the outlet port 206, and a diverter, namely a first diverter 402 having a base portion 502 and a rim 504 and a second diverter 802 having a base portion 804 and a rim 806.

In this embodiment, at least a portion of the base portion 502 of the first diverter 402 is connected to the export end 704 of the inflow tube 702 by a tether 708 and at least a portion of the rim 804 of the second diverter 802 is connected to the intake end 306 of the elongated exit tube 304 by a tether 708. In this embodiment the rim 804 of the second diverter 802 extends beyond the intake end 306 of the elongated exit tube 304.

Figure 9:
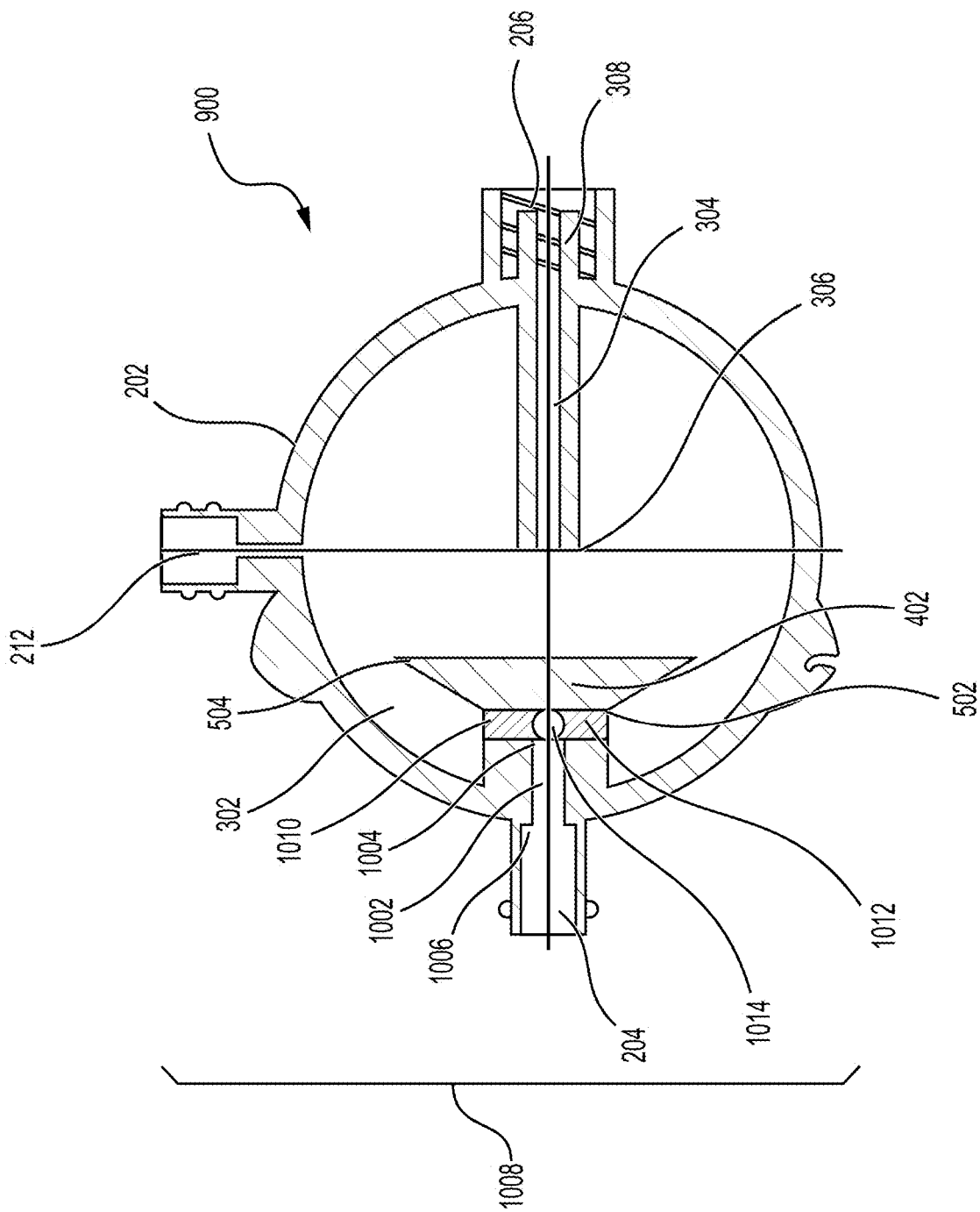
FIG. 9 is a cut through view of an apparatus according to one embodiment of the present invention.

Referring now to FIG. 9, there is provided a cross section view of the apparatus. Parts similar to features hereinbefore described are accorded the same reference number. The apparatus comprises a housing 202 forming a chamber 302, with an inlet port 204 and an outlet port 206, an inflow tube 702 with an export end 704 being centrally located within the chamber 302 and an intake end 706 of the inflow tube 702 being connected to the inlet port 204, an elongated exit tube 304 with the intake end 306 of the elongated exit tube 304 being centrally located within the chamber 302 and the export end 308 of the elongated exit tube 304 being connected to the outlet port 206, and a diverter, namely a first diverter 402. The diverter 402 defines a compartment within the chamber 302, the diverter 402 having a base portion 502 and a rim 504. In this embodiment the export end 704 of the inflow tube 702 abuts the base portion 502 of the diverter 402. The rim 504 of the diverter 402 is positioned between the base portion 502 of the diverter 402 and the intake end 306 of the elongated exit tube 304. In this embodiment the apparatus also comprises a diffuser 902, wherein the diffuser 902 is formed of a plurality of holes. In this embodiment the diffuser 902 comprises at least three holes 904 906 908, the first hole 904 exiting upwards into the chamber 302, the second hole 906 exiting downwards into the chamber 302 and the third hole 908 exiting face on into the chamber 302. While in this embodiment three holes 904 906 908 are shown, it should not be read as limiting the present invention in any way. It is to be appreciated that other variations on the invention may comprise of any number of holes.

In this embodiment the diverter 402 and the intake end 306 of the elongated exit tube 304 are spaced apart, such that the rim 504 of the diverter 402 does not extend beyond the intake end 306 of the elongated exit tube 304.

In this embodiment the apparatus comprises an inflow tube 702, which extends into the chamber and abuts the diffuser 902, the diffuser 902 then abuts the base portion 502 of the diverter 402.

In an alternative embodiment the rim 504 of the diverter 402 may extend beyond the intake end 306 of the elongated exit tube 304. Such a design would further ensure that bubbles remain directed away from the intake end 306 of the elongated exit tube 304. Alternative arrangements of the inflow tube 702 are also possible.

In use, fluid arrives via the inlet port 204 and enters the chamber 302 of the apparatus 900 via the diffuser 902, through the plurality of holes 904 906 908. The bubbles are then diverted, by the first diverter 402, away from the elongated exit tube 304 and towards the outer portions of the chamber 302 of the apparatus 200. The fluid arriving at the diffuser 902 from the inlet port 204 has a first direction of flow; on passing through the diffuser 902 a different direct of flow is imparted. The post diffuser 902 fluid within the chamber 302 has a first direction of fluid flow; on contact with the first diverter 402 a different direction on fluid flow is imparted. The different direction of fluid flow imparted by the diverter 402 generally follows the contours of the diverter 402, resulting in the fluid being pushed towards the outer portion of the chamber 302, along with any entrained gas therein. When the post diffuser 902 fluid within the chamber 302 makes contact with the diverter 402, the fluid velocity is slowed. Slowing of the fluid velocity enables an elongated period of time within which bubbles may move away from the elongated exit tube 304 and towards the outer portions of the chamber 302 of the apparatus 200. Entrained gas in the form of bubbles pass through a volume of fluid within the chamber 302 and friction exerted on the outer surface of the bubble increases resulting in the trajectory being altered, such that buoyancy becomes the dominant force moving the bubble towards the uppermost outer portion of the chamber 302. Fluid, that is now substantially free from bubbles, collects between the diverter 402 and the intake end 306 of the elongated exit tube 304. The fluid substantially free from bubbles locates centrally within the chamber 302 and may be understood to be slower moving than fluid moving along the outer portions of the chamber 302. The fluid substantially free from bubbles is then drawn into the intake end 306 of the elongated exit tube 304 and exits the chamber 302 via the outlet port 206 and away from the apparatus 900.

Figure 10:
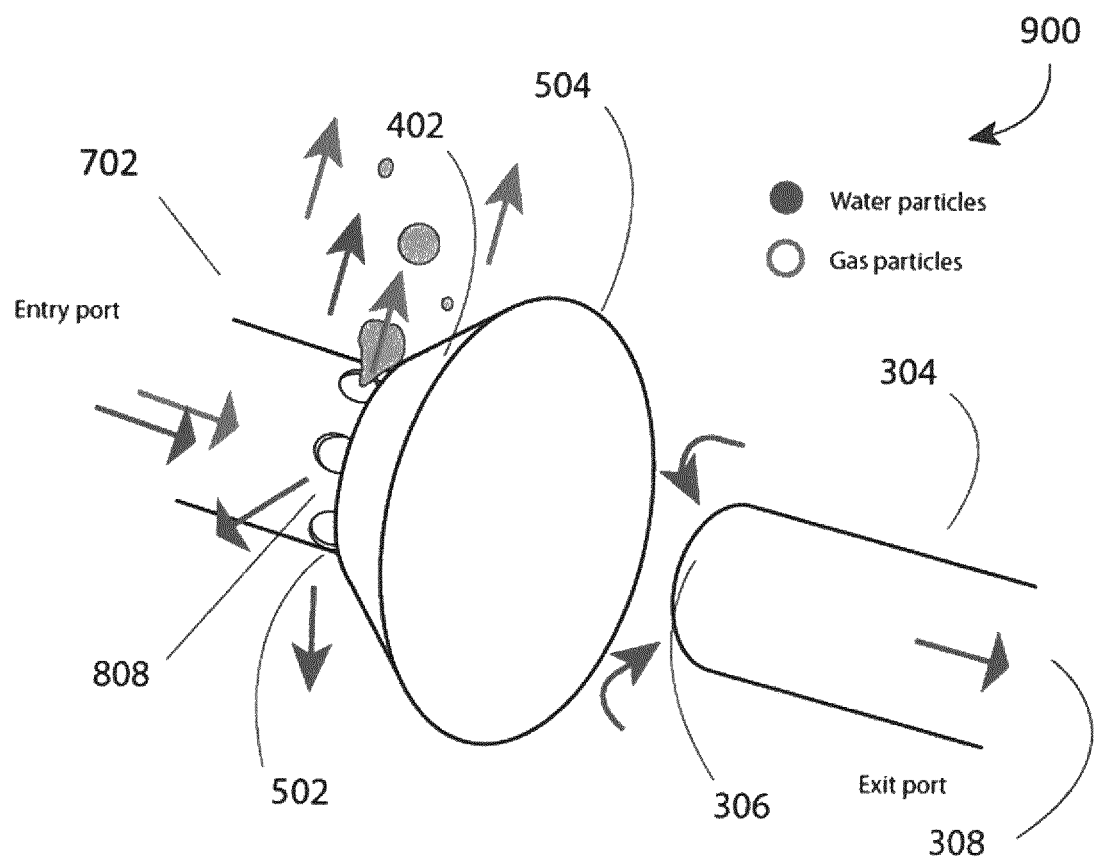
FIG. 10 is a perspective close-up view of the apparatus according to FIG. 9.

Referring now to FIG. 10 there is provided perspective view of the apparatus according to the embodiment of FIG. 9. Parts similar to features hereinbefore described are accorded the same reference number. The apparatus 900 comprises an inflow tube 702, the inflow tube 702 having an export end 704 being centrally located in the chamber 302 and an intake end 706 of the inflow tube 702 being connected to the inlet port 204, a diffuser 902, a diverter 402, the diverter 402 having a base portion 502 and a rim 504, and an elongated exit tube 304, the elongated exit tube 304 having an intake end 306 and an export end 308. The inflow tube 702 is positioned such that it abuts a portion of the diffuser 902 and the diffuser 902 is positioned such that it abuts a portion of the diverter 402.

In this embodiment the diffuser 902 is formed of a plurality of holes spaced apart and positioned in a generally radial arrangement about the circumference of the diffuser 902.

In use, fluid and entrained gas therein arrives at the diffuser 902 via the inflow tube 702. Fluid and entrained gas pass through the plurality of holes of the diffuser 902. Gas bubbles entrained in the fluid generally pass through the uppermost facing holes of the diffuser 902, due to an inherent tendency to rise in an upwards direction, while the remaining fluid passes through any one or more of the holes of the diffuser 902. Once the fluid and entrained gas have passed through the diffuser 902 the fluid and the entrained gas come into contact with the diverter 402. The diverter 402 obstructs the first direction of flow of the fluid and entrained gas and causes a change in direction of the fluid and entrained gas, diverting it away from its original path (or first direction of flow) in a generally outward direction and away from the intake end 306 of the elongated exit tube 304. By obstructing the first direction of flow of the fluid and entrained gas the diverter 402 causes the fluid velocity to slow and thus the entrained gas bubbles also slow. This has the effect of causing a change to the external forces applied to the membrane of the gas bubble, such that buoyancy becomes the dominant force. As buoyancy becomes the dominant force the entrained gas bubbles move in a generally outward and upward direction and away from the intake end 306 of the elongated exit tube 304.

Figure 11:
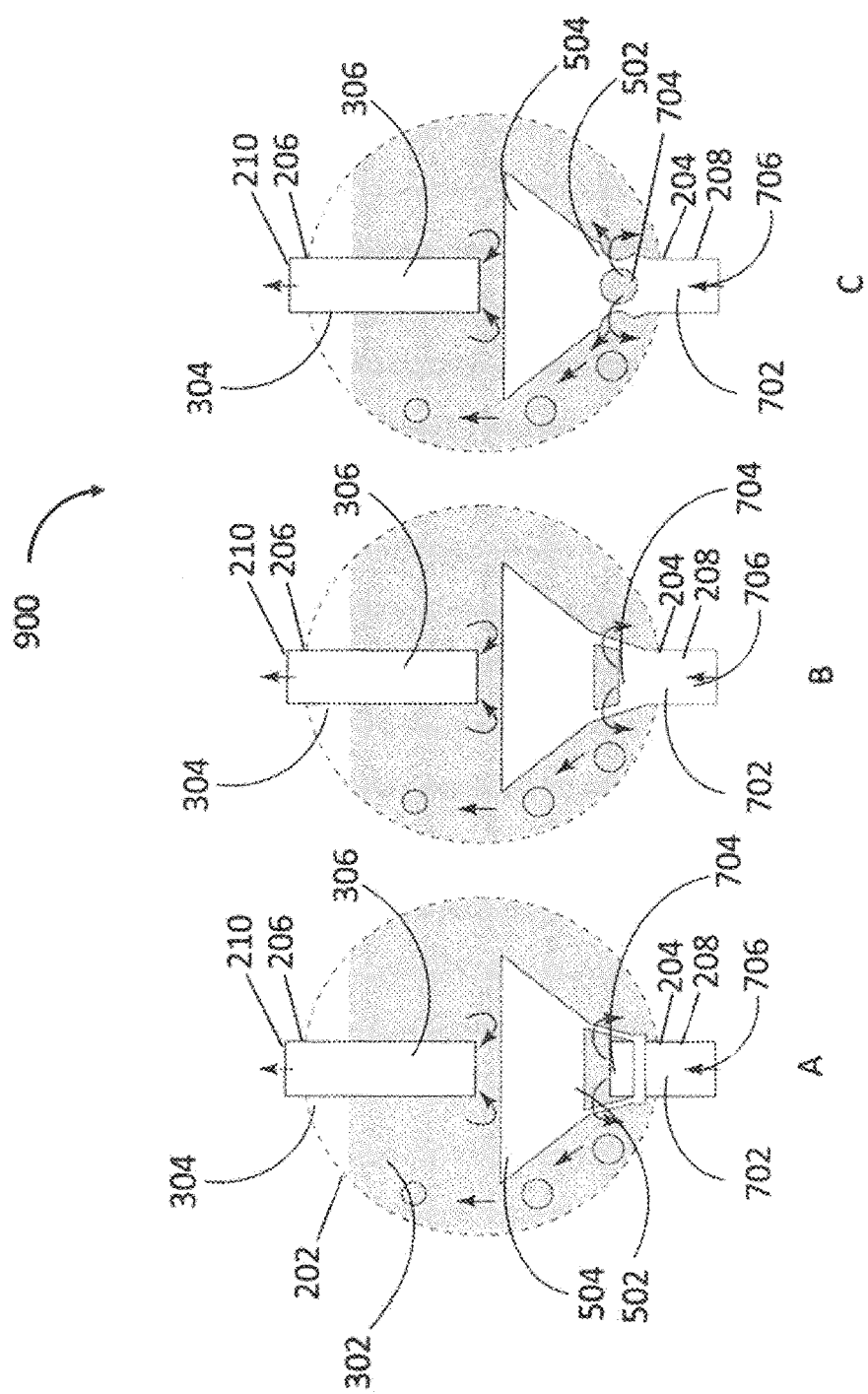
FIG. 11 is a series of diagrammatic views of the apparatus according to FIG. 9.

Referring now to FIG. 11, there is provided an apparatus according to the embodiment of FIG. 10, indicated generally by reference numeral 900. Parts similar to features hereinbefore described are accorded the same reference number. The apparatus 1000 comprises an inflow tube 702, a diffuser 902, a diverter 402, the diverter 402 having a base portion 502 and a rim 504, and an elongated exit tube 304, the elongated exit tube 304 having an intake end 306 and an export end 308.

In FIG. 11A the inflow tube 702 is positioned such that it connected to a portion of the diverter 402 by a tether 708 forming a diffuser 902 comprising at least one hole.

In FIG. 11B the inflow tube 702, diffuser 902 and diverter 402 are integrated forming at least one hole.

In FIG. 11C the inflow tube 702, diffuser 902 and diverter 402 are integrated forming a plurality of holes. In this embodiment three holes can be seen.

Figure 12:
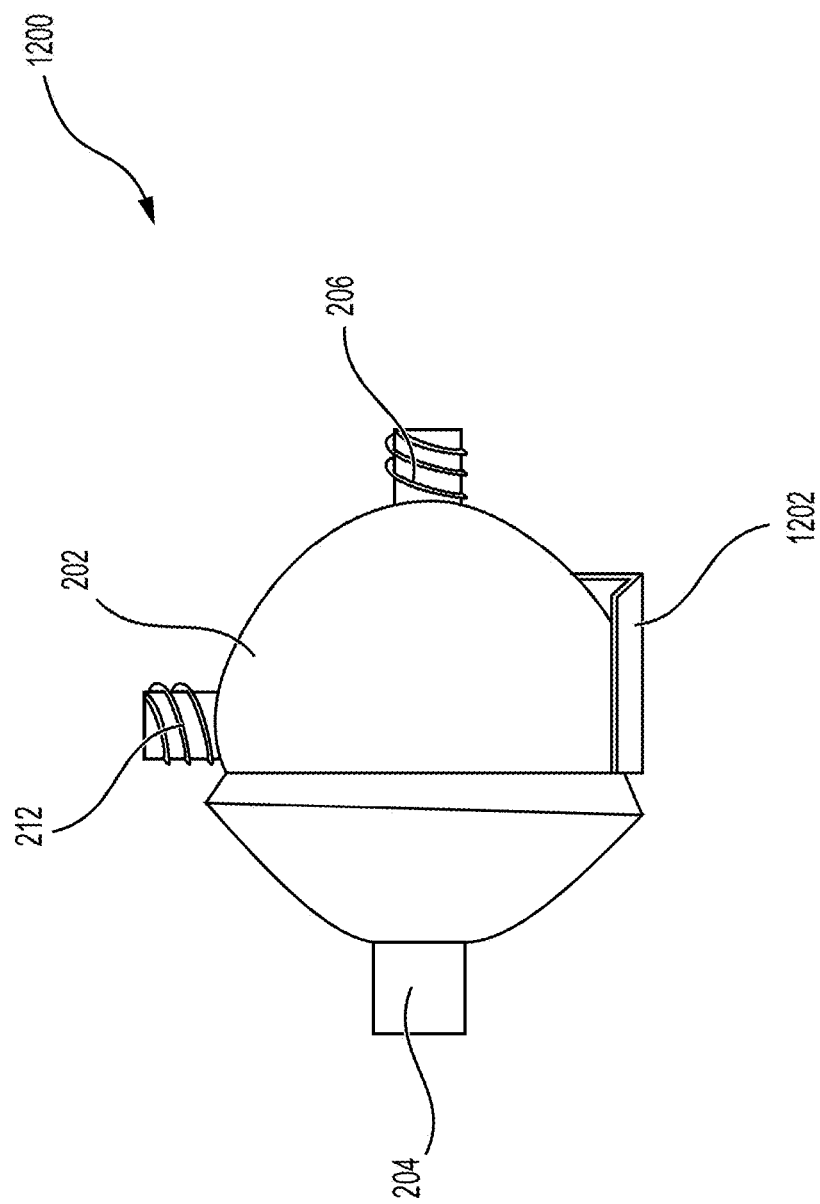
FIG. 12 is a 3D rendered side-on view of the apparatus according to one embodiment the present invention.

Referring now to FIG. 12, there is provided an apparatus according to another embodiment of the invention, indicated generally by reference numeral 1200. Parts similar to features hereinbefore described are accorded the same reference number. The apparatus 1200 comprises a housing 202, an inlet port 204 and an outlet port 206. In this embodiment the apparatus is shown to comprise a venting port 212 and a foot 1202. The foot 1202 is connected to a portion of the housing 202. The foot 1202 may be used to rest the otherwise generally spherical apparatus on a substantially flat surface. Alternatively, the foot 1202 may be used as a means to secure the apparatus to a surface, such as a patient, bed, pillow or any portion of an IV drip set-up 100.

EXAMPLES

Product Need Evaluation

To support product design and development it was determined that further information was required to fully understand the scale of the problem, to evaluate the current limitations in the medical field, and to deliver a more targeted solution.

Method

Figure 13:
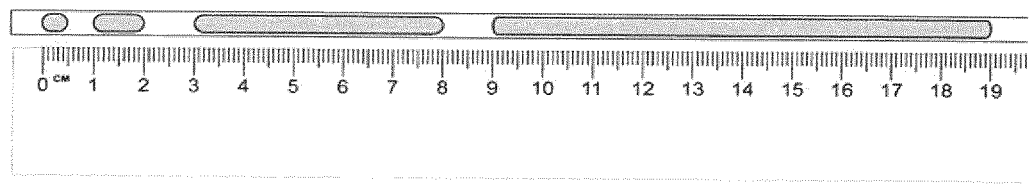
FIG. 13 shows a scale.

A short questionnaire was devised geared towards identifying fear levels and any eventual interest in a solution. Each questionnaire comprised of ten questions, where staff are asked to select the most appropriate statement from a selection. A scale was provided (FIG. 13) and a free-text comment section was also provided.

Fifty questionnaires were disseminated throughout the hospital and a sample of 47 were returned complete, with a proportion being from nurses (56%) and the remainder being doctors (44%) across a variety of departments.

Results

A total of 97% of staff stated that they were moderately or very concerned about bubbles in IV lines. Bubbles are removed by 76% of the staff by opening a port to vent some liquid or manual syringing. A total of 58% of staff stated that removing a bubble is more important than how much fluid is lost in the process.

When asked about concern relating to the size of bubbles, 53% of staff wanted to remove bubbles of up to 5 mm in length. A total of 65% respondents have witnessed bubbles in a medical emergency situation with only 16% of staff stating that they are able to see every bubble in a medical emergency.

Bubbles were also witnessed in fluid warming procedures (54%) as well as non-warmed fluids (44%).

A total of 89% of respondents would use a new bubble trap device some or all of he time to minimize required supervision.

Paediatric care was identified as a high priority.

Conclusion

There is a need for a bubble trap that is capable of reducing the need for constant monitoring, which is also cost effective and easy to use (i.e. minimal training required), reduces associated wastage of fluid materials, can be used in any number of positions and is suitable for use with a variety of infusion procedures, such as but not limited to, parenteral feeding, fluid infusions and heated IV lines.

Proof of Concept

Bubble formation patterns were observed, such as coalescence and pocketing, in response to line placement, height, direction and volume of gas developed. Temperate and flow rate were adjusted to identify the role that each play in the formation of bubbles in an IV line.

In order to observe bubble behaviour in the tubing under various conditions, a typical IV arrangement was setup. Fluids were infused through the tubing under various different flow rate and temperature settings and observations were made of the bubble formations, including; size/volume, location, regularity, behaviours including lodgement and dislodgment, coalescence and other significant behaviours.

Figure 14:
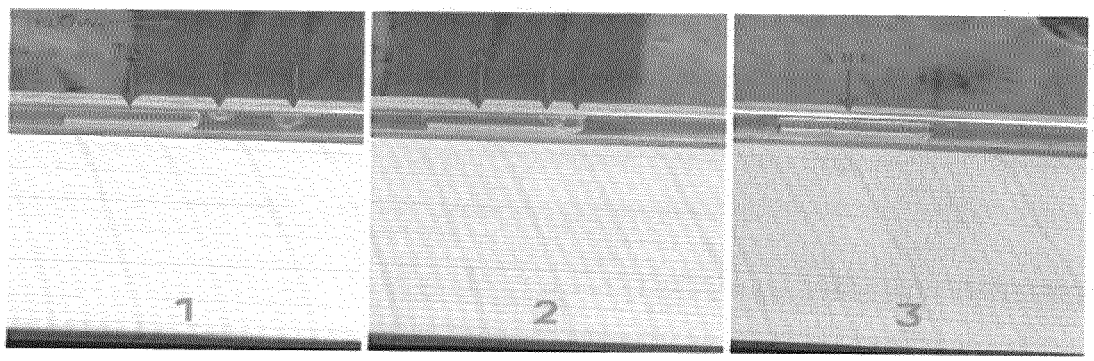
FIG. 14 shows a typical bubble formation pattern in an IV tube and observable characteristics.

FIG. 14 shows a typical bubble formation pattern in an IV tube and observable characteristics. A large bubble (A=8 mm) is shown to travel in the direction of flow. Bubbles (B=1 mm) and (C=2 mm) are observed to be smaller in size and are lodged in a fixed position on the internal wall of the tubing at the locations indicated [pane 1]. The smaller bubbles (B)(C) are collected by the larger bubble (A) and pushed along under force at the front end of the larger bubble (A) [pane 2]. The structure of the bubbles (B)(C) is maintained initially. At a location further along the tube, the bubbles have coalesced into a single bubble (ABC=11 mm) [pane 3]. From the measurement taken it was noted that the volume of the now single bubble (ABC) is now increased. As observed, large or small bubbles of gas will form naturally within an IV tube or similar and the larger bubbles will collect the smaller bubbles as they travel within the fluid stream of the IV tubing. It was also observed (not shown) that smaller bubbles also travel freely within the fluid stream and did not always stick within the tube; however, the observed smaller bubbles tended to stick to the internal tube surface more often. These were dislodged by flicking or movement of the tube and by larger bubbles. It was concluded that the larger bubble was more easily pushed along by the fluid stream.

Figure 15:
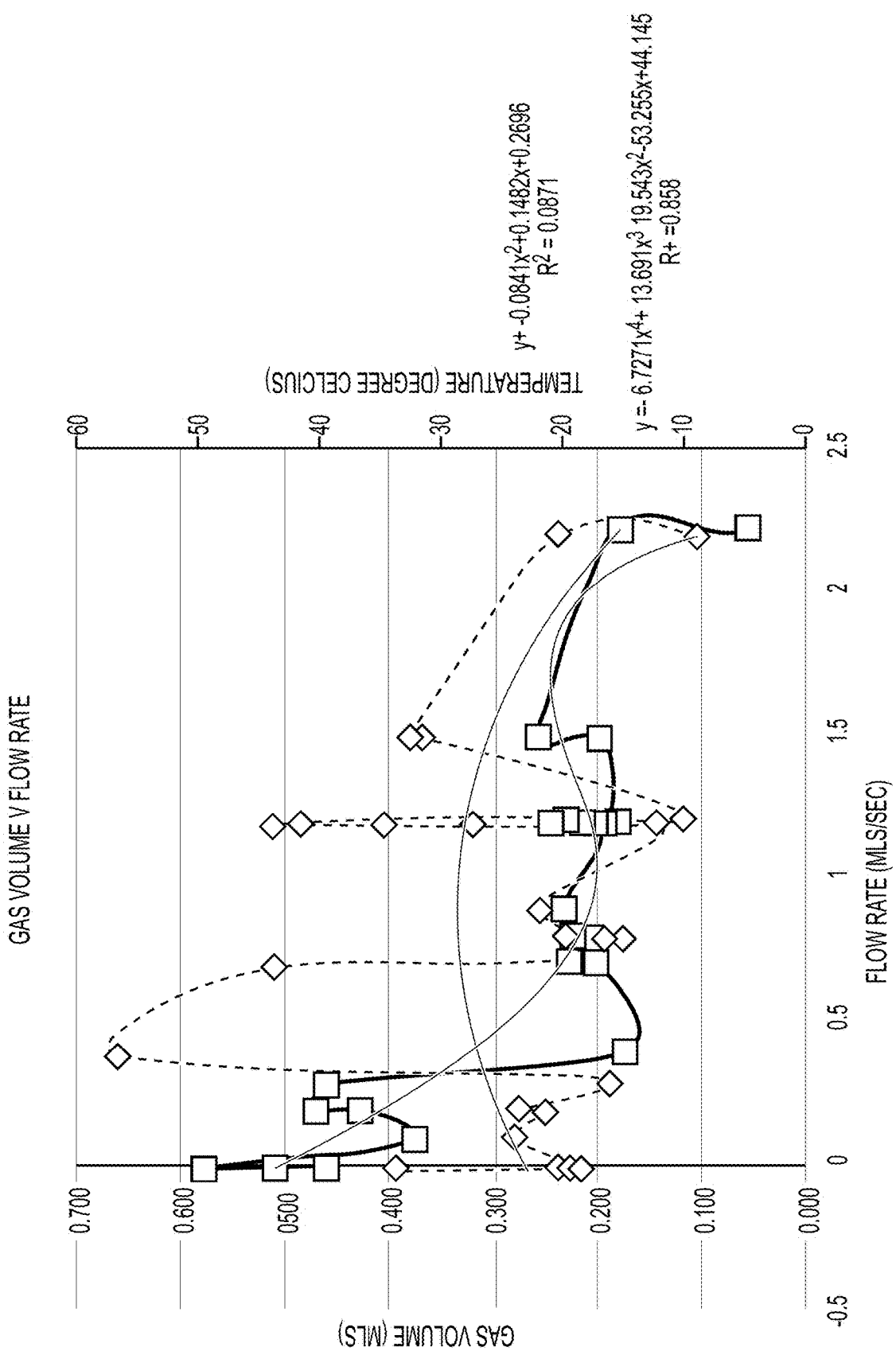
FIG. 15 is a graph showing gas volume in response to temperature and flow rate.

The resulting data was further analysed by plotting the relationship between variables. In FIG. 15 gas volume is shown graphically (square) in relation to temperature of the liquid at starting point. The polynomial trendline of the data was formed, resulting in an order 3 shape due to the two hills or valleys. This indicated that in general, the direction of data points for gas volume seems to be heading upwards as temperature decreased. The resulting reliability factor measuring the reliability factor between x and y values, $R^2$, was shown to be 0.858, which is close to 1 indicating that the values have high levels of linear reliability. This is in keeping with the volume effects by temperature witnessed in the experiments where gas levels increased as temperature of liquids increased.

The Flow Rate vs Gas Volume line of FIG. 15 (diamond) graphically forms a very irregular shape due to the erratic scatter of the values. The trendline for this graph shows a rise and fall hill shape, an order 2 polynomial. The resulting reliability value was 0.087 which shows the data to be unreliable, meaning there is not a reliable prediction based on the linear relationship y=mx+c. This follows the trend shown during testing as the volume of gas developed due to flow rate was determined to not have a pattern that could be easily predicted.

FIG. 5 shows gas volume in response to temperature (square points) and flow rate (diamond points).

Figure 16:
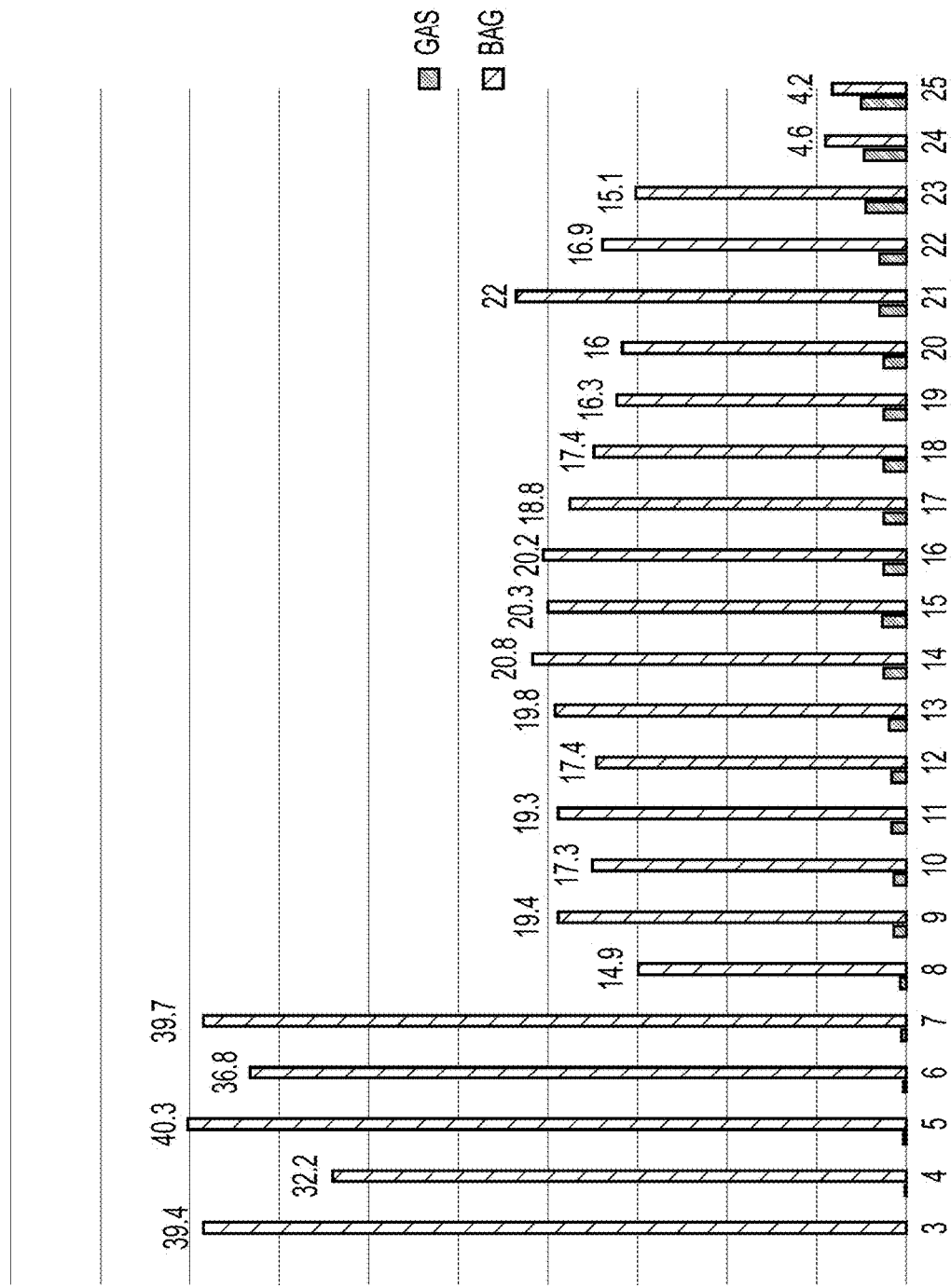
FIG. 16 is a graph showing the correlation of gas volume versus bag temperature.

FIG. 16 shows the correlation of gas volume (dark grey; spotted) versus bag temperature (light grey; diagonal lines).

The highest volume of gas produced (2.4 mls/1000 mls) in these experiments is critical in determining the volume requirements of the device to capture gas from the line reliably. This information helps to validate the time given to the experimental phase.

Prototyping

Standard 3D printing techniques were used to produce the prototype of varying diverter designs. These resulting prototypes then underwent various tests designed to determine suitability of the prototype design, namely reliability and ease of use.

360 Orientation Testing

Product need evaluation confirmed that the bubble trap must operate effectively through a complete range of orientations and motions due to IV lines being regularly moved during various procedures. The prototypes were therefore tested in all orientations through 360 degrees, showing capacity to retain gas far in excess of the maximum degassing volumes indicated through experimentation.

Volume degassing capacity studies were conducted using heated fluids since incidence of degassing is more prevalent in heated systems, than would be observed in a non-heated system.

The maximum level was determined from testing where a maximum reading of 2.4 ml/1000 ml was taken with a built-in factor of 5× an average reading was calculated to allow at least a 15 ml gas capacity, for safety reasons. As such the apparatus can collect up to 15 mls of gas before gas levels reach a level where the apparatus will no longer function effectively and before the gas level reaches the elongated exit tube. This means that up to 5 bags of fluids could be infused concurrently at maximum degassing levels.

Depending on the procedure the recommended gas level can vary from zero (e.g. no gas is preferred in Paediatrics due to reduced blood volume and natural 'hole-in-the-heart' present in infants) to 3 ml/kg of body weight in healthy adults (tests conducted on animals) with adverse effects possible from 1 ml/kg of air injected. There are many conflicting reports and it is generally accepted that the body can tolerate some gas (if there are no underlying conditions) in ideal conditions but it is preferable to have no gas enter any patient, if possible. Recent studies cite damage to the Endothelial Glycocalyx layer of the vasculature as a reason to prevent gas bubbles from entering the venous system.

Method

The tap on the IV line is closed and the hotline L1 remains off throughout the whole experiment so as to avoid unwanted gas production that would otherwise hinder the experiment. The IV drip bag is hung from the top of the IV stand and connected to the IV line. The prototype undergoing testing is connected to the end of the lumen line closest to the patient and the extension line is connected to the other end of the prototype. The clave connector is then attached to the gas extraction port. Lines are drawn on a piece of paper with angles of 45, 90, 180, 225, 270, 315 and 360 degrees and the piece of paper is attached to a flat vertical surface. A plastic container is filled with water. A small graduated cylinder is filled with water, making sure that the graduated cylinder is connected to the plastic container using an attachment. The end of the extension line is placed into the graduated cylinder, before the graduated cylinder is rapidly turned upside down into the plastic container so that no liquid escapes the cylinder and the graduated cylinder attachment rests perfectly on the rim of the container ensuring that the cylinder remains vertical during the experiment. The initial reading (zero) of gas on the upside down graduated cylinder is read and recorded. The tap is then turned on to allow liquid to flow from the bag ensuring that it is at the maximum possible flow rate. Gas trapped in the chamber of the prototype undergoing testing is removed using a syringe inserted via the clave connector. Once all the gas has been extracted the prototype section of the line is attached to the flat vertical surface so that it is parallel to the 45 degree angle line previously drawn on the paper. The syringe is filled with 1 ml of air and injected into the IV line next to the hotline L1 so that the gas flows towards the prototype. Gas passing through the prototype into the extension line is observed and the value of gas gathered in the graduated cylinder is recorded. If no gas is observed, then the value is recorded as 0. The experiment is repeated for volumes of air up to 20 ml going up in increments of 1 ml and then for each of the following angles: 90, 180, 225, 270, 315 and 360 degrees.

The terms "comprise" and "include", and any variations thereof required for grammatical reasons, are to be considered as interchangeable and accorded the widest possible interpretation.

It will be understood that the components shown in any of the drawings are not necessarily drawn to scale, and, like parts shown in several drawings are designated the same reference numerals.

It will be further understood that features from any of the embodiments may be combined with alternative described embodiments, even if such a combination is not explicitly recited hereinbefore but would be understood to be technically feasible by the person skilled in the art.

The invention is not limited to the embodiments hereinbefore described which may be varied in both construction and detail.

While the invention is described in the context of use in an IV drip set-up, a device of the present invention may be adapted for use in other applications, such as but not limited to, use in blood transfusion apparatus and any other fluid treatment set-up where entrained gas requires removing, capturing or expelling.

The invention claimed is:

1. A medical apparatus suitable for separating and collecting gas bubbles entrained in a fluid, wherein the apparatus comprises:
    a housing (202) defining at least one chamber, the chamber having an inlet port (204) and an outlet port (206);
    a medical inflow tube (702) with an intake end and an export end, the export end being located within the chamber;
    a diverter (402) positioned between the chamber inlet port and the chamber outlet port, wherein the diverter comprises a base portion (502) and a rim (504);
    an exit tube (210) with an intake end (306) and an export end (308), wherein said intake end (306) of the exit tube is located within the chamber and said export end of the exit tube is connected to the outlet port (206) of the chamber; and
    the diverter being integrated with a diffuser (704) in the medical inflow tube (702) between the inlet port and the diverter, wherein the diffuser comprises at least one hole in the medical inflow tube (704), and is configured to impart an alternative direction of movement of fluid entering the chamber in the medical inflow tube; and
    wherein the diffuser and the diverter are configured so that bubbles in an inflow fluid, under fluid flow parameters, move through the at least one hole of the diffuser and into the chamber and are then guided by the diverter towards the outer portions of the chamber and away from the intake end of the elongated exit tube.

2. The apparatus of claim 1, wherein the diffuser comprises a plurality of holes (704) in the medical inflow tube.

3. The apparatus according to claim 1, wherein the diffuser comprises a plurality of holes in the medical inflow tube, the plurality of holes being spaced apart and positioned in a generally radial arrangement about a circumference of the diffuser.

4. The apparatus according to claim 1, wherein the diffuser is configured to slow the velocity of fluid arriving from the medical inflow tube into the chamber.

5. The apparatus of claim 1, wherein a portion of the medical inflow tube (208) abuts the diverter or is integral with the diverter.

6. The apparatus according to claim 1, wherein the diverter has a frustoconical shape such that a diameter of the diverter at the rim portion is greater than the diameter of the diverter at the base portion, the base portion being positioned nearer the medical inflow tube than the rim portion.

7. The apparatus according to claim 1, comprising at least one venting port suitable for purging trapped gas bubbles from the apparatus.

8. The apparatus according to claim 1, comprising at least one venting port suitable for purging trapped gas bubbles from the apparatus; and
    wherein the venting port is coupled with a release means, the release means being operable to move between a closed position to an open position; such that, in use, when the release means is in the open position the trapped gas is purged from the chamber of the apparatus through the venting port.

9. The apparatus according to claim 1, comprising at least one venting port suitable for purging trapped gas bubbles from the apparatus; and wherein the venting port is coupled with a release means, the release means being operable to move between a closed position to an open position such that, in use, when the release means is in the open position the trapped gas is purged from the chamber of the apparatus through the venting port; wherein the release means is automated.

10. The apparatus according to claim 1, comprising at least one venting port suitable for purging trapped gas bubbles from the apparatus; and
    wherein the venting port comprises a gas permeable-water impermeable membrane such that, in use, trapped gas traverses the gas pervious/water impervious membrane and is purged from the chamber, while water is retained within the chamber of the apparatus.

11. The apparatus according to claim 1, wherein the chamber is spherical.

12. The apparatus according to claim 1, wherein the apparatus is arranged in a circuit.

13. The apparatus according to claim 1, wherein the apparatus comprises a plurality of chambers arranged in a series.

14. The apparatus according to claim 1, wherein the chamber and the diverter have an internal surface which has a surface treatment for hydrophilic control of a bubble and its movement within the chamber.

15. The apparatus according to claim 1, wherein the rim of the diverter surrounds the intake end of the exit tube.

16. The apparatus according to claim 1, wherein the apparatus comprises a gas-impermeable and liquid-permeable membrane at the intake end of the exit tube.

17. The apparatus according to claim 1, wherein the apparatus comprises a filter to remove particulates before entry of liquid to the intake end of the exit tube.

18. An intravenous line kit comprising:
    at least one intravenous drip bag;
    at least one drip chamber;
    at least one supply tube having a proximal end and a distal end;
    a bubble trap;
    a fluid flow control means;
    at least one clamp; and
    a cannula;
    wherein the bubble trap comprises:
        a housing defining at least one chamber, the chamber having an inlet port and an outlet port;
        medical inflow tube with an intake end and an export end, the export end being located within the chamber;

a diverter positioned between the chamber inlet port and the chamber outlet port, wherein the diverter comprises a base portion and a rim;

an exit tube with an intake end and an export end, wherein said intake end of the exit tube is located within the chamber and said export end of the exit tube is connected to the outlet port of the chamber; and the diverter being integrated with a diffuser in the medical inflow tube between the inlet port and the diverter, wherein the diffuser comprises at least one hole in the medical inflow tube, and is configured to impart an alternative direction of movement of fluid entering the chamber in the medical inflow tube.

19. A medical apparatus suitable for separating and collecting gas bubbles entrained in a fluid, wherein the apparatus comprises:

a housing defining at least one chamber, the chamber having an inlet port and an outlet port;

a medical inflow tube with an intake end and an export end, the export end being located within the chamber;

a diverter positioned between the chamber inlet port and the chamber outlet port, wherein the diverter comprises a base portion and a rim;

an exit tube with an intake end and an export end, wherein said intake end of the exit tube is located within the chamber and said export end of the exit tube is connected to the outlet port of the chamber; and the inflow tube connected to the diverter by one or more tethers, the one or more tethers forming a diffuser in the medical inflow tube between the inlet port and the diverter, wherein the diffuser is configured to impart an alternative direction of movement of fluid entering the chamber in the medical inflow tube.

* * * * *